United States Patent

Meanwell et al.

[11] Patent Number: 4,668,686
[45] Date of Patent: May 26, 1987

[54] IMIDAZOQUINOLINE ANTITHROMBROGENIC CARDIOTONIC AGENTS

[75] Inventors: Nicholas Meanwell, Mt. Vernon; John J. Wright, Evansville, both of Ind.

[73] Assignee: Bristol-Myers Company, New York, N.Y.

[21] Appl. No.: 832,212

[22] Filed: Feb. 26, 1986

Related U.S. Application Data

[63] Continuation-in-part of Ser. No. 726,869, Apr. 25, 1985.

[51] Int. Cl.⁴ .................. A61K 31/395; C07D 471/04
[52] U.S. Cl. ........................ 514/293; 546/82
[58] Field of Search ........................ 546/82; 514/293

[56] References Cited

PUBLICATIONS

Chem. Abstracts, vol. 102, 1985, 132000j.
Reid, et al., Chem. Ber., 1956, 89, 2684–2687.
J. S. Fleming, et al., New Drugs Annual: Cardiovascular Drugs, Raven Press, pp. 277–294, New York (1983).
Slouka, et al., Synthesis of 1,2,4-Triazino[5,6-b] and Imidazo [4,5-b]quinoline Derivatives, pp. 2628–2634, Coll. Czech. Chem. Commun. 49 (1984).

*Primary Examiner*—John M. Ford
*Assistant Examiner*—J. Richter
*Attorney, Agent, or Firm*—Robert H. Uloth

[57] ABSTRACT

Novel series of 1,3-dihydro-2H-imidazo[4,5-b]quinolin-2-ones of the Formula

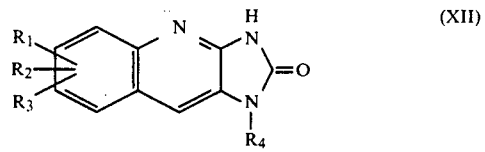

(XII)

wherein $R_1$ is halogen, lower alkyl, lower alkoxy, trifluoromethyl; $R_2$ is hydrogen, halogen, lower alkyl, lower alkoxy; $R_3$ is hydrogen, halogen, lower alkyl, lower alkoxy; and $R_4$ is hydrogen or lower alkyl. The compounds are therapeutically useful as inhibitors of blood platelet aggregation and/or as cardiotonic agents.

34 Claims, No Drawings

IMIDAZOQUINOLINE ANTITHROMBROGENIC CARDIOTONIC AGENTS

CROSS REFERENCE TO RELATED APPLICATION

This is a continuation-in-part application of Ser. No. 726,869, filed Apr. 25, 1985.

BACKGROUND OF THE INVENTION

This invention generally pertains to heterocyclic carbon compounds having drug and bio-affecting properties and to their preparation and use. In particular, the invention is concerned with a series of new 1,3-dihydro-2H-imidazo[4,5-b]quinolin-2-one derivatives which are phosphodiesterase inhibitors, blood platelet antiaggregators and cardiotonic agents.

As a structural class, applicants are aware of relatively few 1,3-dihydro-2H-imidazo[4,5-b]quinolin-2-ones with the following chemical literature illustrative of the art.

Kozak, et al., *Bull. Intern. Acad. Polanaise,* 1930A, 432–438 (Chem. Abs., 25, 5400) describes the unsubstituted compound 1,3-dihydro-2H-imidazo[4,5-b]quinolin-2-one of formula (1).

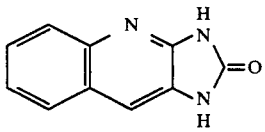

Musial, *Roczniki Chem.,* 1951, 25, 46–52 (Chem. Abs., 1953, 47, 4885f) synthesized 1,3-derivatives of (1) as illustrated in formula (2).

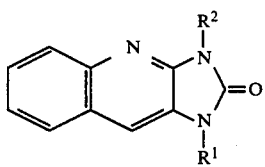

$R^1$ = Br, $NO_2$, $NH_2$
$R^2$ = H, Br

Fryer, et al., *J. Org. Chem.,* 1977, 42, 2212–2219 describes the 3,7,9-trisubstituted compound of formula (3).

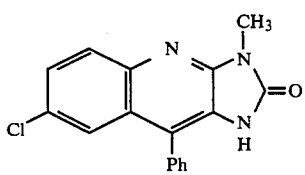

Reid, et al., *Chem. Ber.,* 1956, 89, 2684–2687 describes the synthesis of the 1,3-diphenyl derivative of formula (4).

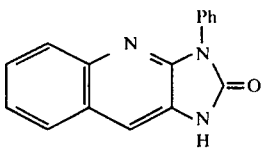

No pharmacological utility is taught for the 1,3-dihydro-2H-imidazo[4,5-b]quinolin-2-one structures disclosed in the aforementioned references which are of a chemical nature.

Various derivatives of the tetrahydroimidazo[2,1-b]quinozolin-2-one (5) heterocycle have been studied for their platelet inhibition and cardiotonic properties.

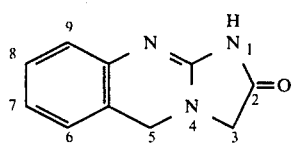

For example:

Beverung, Jr., et al., U.S. Pat. No. 3,932,407 disclose a series of compounds useful as blood platelet antiaggregative and/or antihypertensive and/or bronchodilator agents of the tetrahydroimidazo[2,1-b]quinazolin-2-one class. Anagrelide (6), a particularly preferred member of the Beverung, Jr., et al. series, has been studied extensively, e.g., J. S. Fleming, et al., *New Drugs Annual: Cardiovascular Drugs,* Raven Press, pages 277–294, New York (1983).

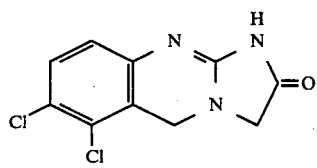

Chodnekar, et al., U.S. Pat. No. 4,256,748 describes a series of compounds of the formula (7) as inhibitors of the aggregation of blood platelets and cardiotonic activity.

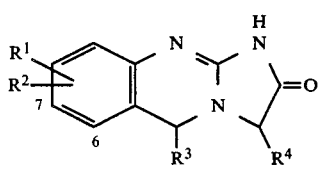

Representative of the Chodneker compounds are RO 14-2525 ($R^4$=$CH_3$, $R^3$=H, $R^2$=6-$CH_3$, $R^1$=7-Br) and RO 13-6438 ($R^4$=$CH_3$, $R^3$=H, $R^2$=6-$CH_3$, $R^1$=H).

SUMMARY OF THE INVENTION

In its broadest aspect, this invention is concerned with a new series of 1,3-dihydro-2H-imidazo[4,5-b]quinolin-2-ones having valuable pharmacological properties which makes them particularly useful as cardiotonic agents and/or inhibitors of phosphodiesterase and mammalian blood platelet aggregation. Formula I and Formula XII (infra.) illustrate the compounds of the invention and the ring numbering system used herein.

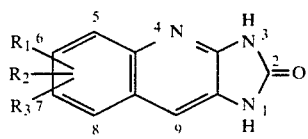

In the foregoing formula, $R_1$ is halogen, lower alkyl, lower alkoxy; $R_2$ is hydrogen, halogen, lower alkyl, lower alkoxy; and $R_3$ is hydrogen, halogen, lower alkyl, lower alkoxy. Another embodiment of the invention relates to pharmaceutically acceptable compositions comprised of a Formula I or Formula XII (infra.) compound combined with at least one pharmaceutically acceptable excipient. A further embodiment of this invention relates to a method for inhibiting phosphodiesterase and blood platelet aggregation in a mammal which comprises administering a therapeutically effective amount of a compound of Formula I or Formula XII (infra.) or a pharmaceutically acceptable salt thereof to a mammal in need of such treatment. A still further embodiment of this invention relates to a method for increasing heart inotropic activity which comprises administering a therapeutically effective amount of a compound of Formula I or Formula XII (infra.) or a pharmaceutically acceptable salt thereof to a mammal in need of such treatment.

DETAILED DESCRIPTION OF THE INVENTION

The compounds of the instant invention comprise those of Formula I

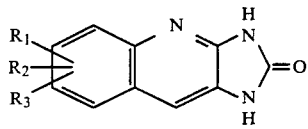

wherein $R_1$ is halogen, lower alkyl, lower alkoxy;

$R^2$ is hydrogen, halogen, lower alkyl, lower alkoxy;

$R_3$ is hydrogen, halogen, lower alkyl, lower alkoxy;

or a pharmaceutically acceptable salt thereof.

As used herein, the term "halogen" or "halo" comprehends flourine, iodine, and most preferably bromine and chlorine; the term "lower alkyl" refers to a branched or unbranched saturated hydrocarbon chain containing from 1 to 4 carbon atoms; for example, methyl, ethyl, n-propyl, isopropyl, n-butyl, tert.-butyl, and the like. The terms "alkyl of 1 to 4 carbon atoms" and "lower alkyl" are used interchangeably with specific terms represented by conventional symbols, i.e., Me=$CH_3$, Et=$C_2H_5$, etc.

The term "lower alkoxy" comprehends ethers containing from 1 to 4 carbon atoms as defined for alkyl; such as methoxy, ethoxy, isopropoxy, tert.-butoxy, and the like.

According to the present invention, the compounds characterized by Formula I

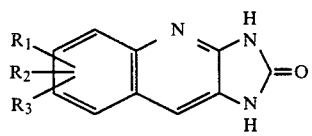

wherein $R_1$ is halogen, lower alkyl, lower alkoxy; $R_2$ is hydrogen, halogen, lower alkyl, lower alkoxy; and $R_3$ is hydrogen, halogen, lower alkyl, lower alkoxy are obtained by a process comprising (a) reducing a substituted hydantoin of Formula II

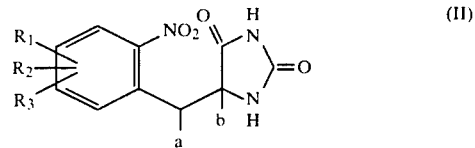

wherein a and b are hydrogen or together are a covalent bond, $R_1$, $R_2$, and $R_3$ are defined as above; and (b) treating the reduced material with an oxidant such as iodine when required.

The reduction of Formula II hydantoin intermediates is carried out by conventional chemical or catalytic methods. For instance, the Formula II hydantoins can be chemically reduced by treatment with hydrogen iodide and red phosphorus according to the method of Kozak, et al., supra. Catalytic hydrogenation is particularly preferred and accomplished with a transition metal catalyst, preferably palladium-on-carbon, in an appropriate reaction inert solvent such as dimethylformamide. Reduction is carried out at room temperature and when hydrogen uptake is essentially complete, the reaction mixture is warmed and filtered or optionally heated to about 100° C. for a 1 to 4 hour period before filtering. In some instances, residual material obtained by concentrating the filtrate predominantly consists of the desired Formula I product produced by facile cyclization and aratomization to the fused quinoline ring system. In other instances, the residual material predominantly consists of the uncyclized Formula IIA amino hydantoin (wherein a and b, $R_1$, $R_2$, $R_3$ are as defined above) resulting from reduction of the Formula II nitro hydantoin or the 4,5-dihydroquinoline intermediate of Formula IIB (wherein $R_1$, $R_2$ and $R_3$ are defined as above). In other instances, the residual material predominantly consists of a mixture of Formula IIA, IIB intermediates together with the desired Formula I product. Without being bound by theory, the transformation of a Formula II nitro-hydantoin to the Formula I product is thought to involve reduction of the nitro group and olefenic double bond to the corresponding Formula IIA amine (wherein a and b are hydrogen). Ring cyclization follows or occurs simultaneously to the Formula I product or the 1,3,9,9a-tetrahydroquinoline intermediate of Formula IIB which is aromatized by dehydrogenation.

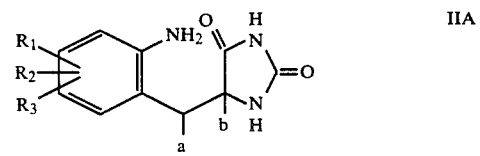

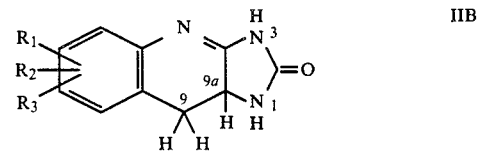

In those cases where the reaction is incomplete, the residual material is treated with an oxidant such as iodine in an alkanol solvent such as methanol or dimethylformamide and the like at reflux temperature. Under these conditions, cyclization of Formula IIA amines to the Formula I products or the Formula IIB tetrahydroquinoline intermediates with oxidation of the latter to the desired 1,3-dihydro-2H-imidazo[4,5-b]quinolin-2-ones of Formula I is effected. The Formula IIA and IIB compounds are considered part of the instant invention. When iodine is employed, the Formula I product is isolated in base form by sequentially treating the reaction mixture with aqueous sodium thiosulfate and alkali metal carbonate such as sodium carbonate. Conversion of the base form to pharmaceutically acceptable acid addition salts is carried out by conventional means.

The pharmaceutically acceptable acid addition salts of the instant invention are those in which the anion does not contribute significantly to the toxicity or pharmacological activity of the salt and, as such, they are the pharmacological equivalents of the bases of Formula I and Formula XII (infra.). They are generally preferred for medical usage. In some instances, they have physical properties which makes them more desirable for pharmaceutical formulation purposes such as solubility, lack of hygroscopicity, compressibility with respect to tablet formation and compatibility with other ingredients with which the substance may be used for pharmaceutical purposes. As stated above, the salts are conventionally prepared, for instance by treating a Formula I for Formula XII (infra.) base with the selected acid preferably in solution. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include hydrochloric, hydrobromic, hydroiodic, citric, acetic, propionic, benzoic, mandelic, sulfuric, phosphoric, nitric, mucic, isethionic, methanesulfonic, ethanesulfonic, p-toluene sulfonic, palmitic, heptanoic, and others.

The Formula II hydantoins wherein a and b are hydrogen employed in the process for preparing the instant compounds can be prepared according to procedures described by Connors, et al., *J. Chem. Soc.*, 2994–3007 (1960) illustrated in the following reaction scheme.

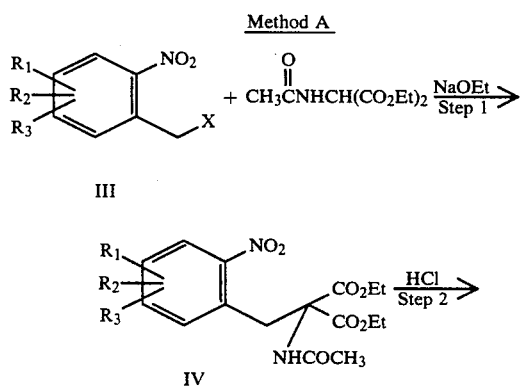

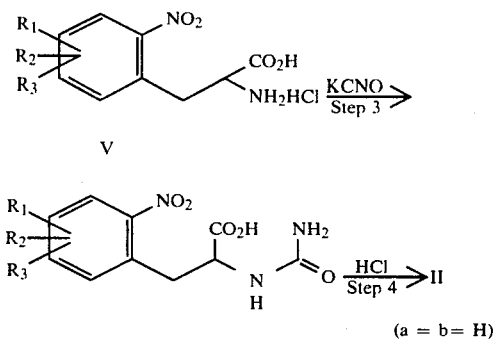

In Method A, the "X" symbol in Formula III intermediates represents a suitable leaving group such as mesylate, tosylate, phosphate, sulfate and halogen, preferably chlorine or bromine. Such compounds are commercially available or can be obtained by methods known to the art. For example, the Formula III intermediate 2,3-dimethyl-6-nitrobenzylchloride can be prepared from 2,3-dimethyl-6-nitroaniline by conventional methods according to the following scheme.

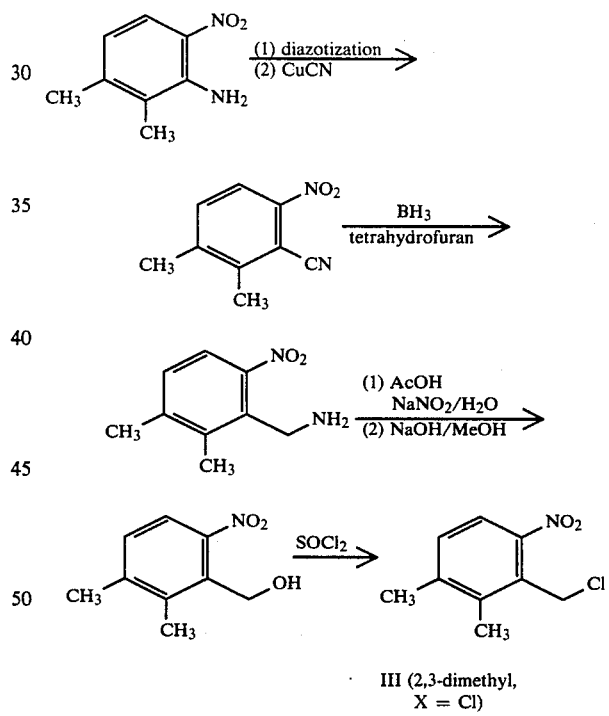

The 2,3-dimethyl-6-nitrobenzyl alcohol precursor to the benzyl chloride (III) can readily be esterified to further provide Formula III intermediates such as the mesylate, tosylate, phosphate, sulfate and the like. In step 1 of Method A, benzyl-X starting material (III), e.g., orthonitro-$R_1,R_2,R_3$-substituted benzyl chloride, is condensed with diethyl acetamidomalonate in a reaction inert solvent such as ethanol, methanol, n-propanol, acetonitrile, dimethylformamide in the presence of a suitable alkali metal base such as sodium ethoxide, sodium hydroxide, sodium carbonate and the like, at temperatures ranging from 50° to 150° C. to provide the diethyl-alpha-acetamido-2-nitrobenzylmalonate intermediates of Formula IV. The reaction period varies to some extent depending on solvent, alkali metal salt and temperature selected. In the case of sodium ethoxide in ethanol, the reaction is carried out at reflux temperature for a period of 1 to 24 hours. In step 2, the phenylalanines of Formula V are obtained by refluxing the benzylmalonate esters (IV) in a strong acid such as 50% hydrochloric acid. In step 3, the phenylalanine (V) is treated with potassium cyanate at about 100° C. and the mixture acidified to provide the aminocarbonyl phenylalanine Formula VI intermediates. In step 4, the Formula VI intermediates are cyclized to the substituted hydantoins of Formula II wherein a and b are hydrogen. Cyclization to the hydantoin intermediates is effected under acid conditions, for instance with 50% hydrochloric acid at 100° C. or by refluxing in ethanol with hydrogen chloride.

Formula II (wherein a and b are hydrogen) hydantoins can also be obtained according to the method illustrated in the following reaction scheme.

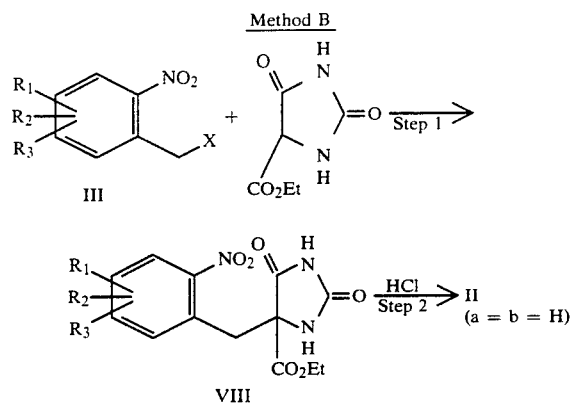

Method B involves alkylating the sodium salt of ethyl hydantoin-5-carboxylate with a Formula III benzyl intermediate followed by hydrolytic decarboxylation of the alkylated intermediate. In Step 1, the Formula III benzyl intermediate is reacted with ethyl sodiohydantoin-5-carboxylate (VII) in a reaction inert solvent. Suitable solvents include alcohols such as methanol, ethanol, propanol, isopropanol and the like as well as other solvents generally used in alkylating reaction such as acetonitrile, dimethylformamide and the like. In addition to the sodium salt of the hydantoin ester which is preferred, other strong alkali salts such as potassium and lithium are operable. Conversion of the Formula VIII hydantoin-5-carboxylate intermediates to the Formula II hydantoins is effected under conventional hydrolysis and decarboxylation conditions such as heating the hydantoin of Formula VIII with 50% hydrochloric acid.

The Formula II hydantoins wherein a and b together represent a covalent bond can be prepared according to procedures described by Billek, Monatsh, 1961, 92, 352–360 (Chem. Abs., 1962, 56, 394b) illustrated in the following reaction scheme.

Method C

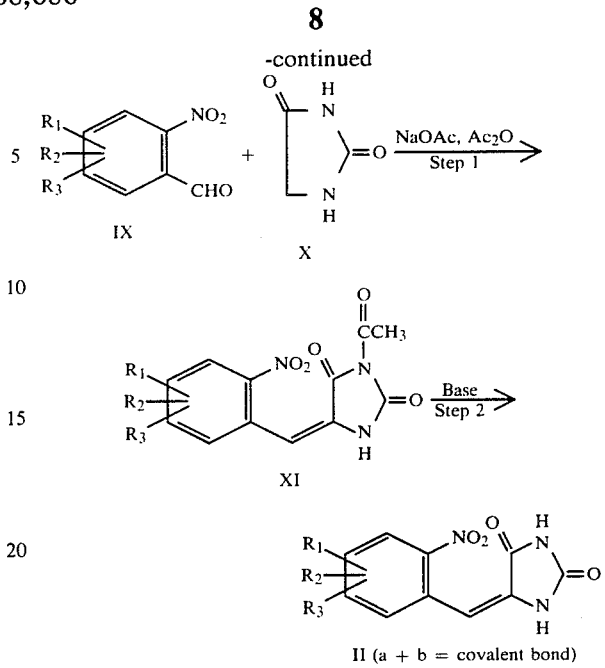

Method C involves condensation of a substituted benzaldehyde of Formula IX with hydantoin (X) in the presence of fused sodium acetate in acetic anhydride at elevated temperatures (e.g., 100°–160° C.). Hydrolysis of the N-acetyl intermediate (XI) obtained in Step 1 is conventionally carried out with an alkali metal hydroxide such as sodium hydroxide to provide the benzylidine hydantoin of Formula II wherein a and b together form a covalent bond.

As stated above, the Formula I compounds or pharmaceutically acceptable salts thereof have pharmacological properties which make them particularly useful as phosphodiesterase inhibitors, blood platelet antiaggregators and/or cardiotonic agents. Regarding the latter, compounds of the invention selectively strengthen myocardial contraction force by which the heart ventricles pump blood into the periphery. Thus, the instant compounds are useful in the curative or prophylactic treatment of cardiac conditions such as myocardial failure where an increase in positive inotropic activity is desirable. Preferred compounds increase contractile force without unduly increasing heart rate.

Platelet aggregation is considered part of a complex physiological mechanism for formation of a thrombus in the vascular system. Thromboembolic phenomena, i.e., the formation of thrombi, are involved in hemostasis and a number of diseased states in mammals including thrombophlebitis, phlebothrombosis, cerebral thrombosis, coronary thrombosis and retinal vessel thrombosis. An increase in propensity for platelet aggregation, sometimes referred to as platelet adhesiveness, is observed following parturition, surgical operations such as coronary artery bypass surgery, organ transplant, angioplasty, prosthetic heart valve implants to name a few; and in ischaemic heart disease, atherosclerosis, multiple sclerosis, intracranial tumors, thromboembolism, and hyperlipemia; refer to A. Poplawski, et al., J. Atherosclerosis Research, 8, 721 (1968). Thus, the compounds of the invention which have antithrombogenic (inhibit blood platelet aggregation) and phosphodiesterase inhibition properties are useful in prevention or treatment of conditions involving platelet aggregation and thrombosis such as the above. Literature relating to prophylactic and therapeutic activities of phosphodiesterase inhibiting compounds include the following: S. M. Amer, "Cyclic Nucleotides as Targets For Drug Design," *Advances in Drug Research*, Vol. 12, 1977, Academic Press, London, pp 1–38; I. Weinryh, et al., *J. Pharm. Sci.*, pp 1556–1567 (1972); S. M. Amer, et al., *J. Pharm. Sci.*, Vol. 64, pp 1–37 (1975); and D. N. Harris, et al., *Enzyme Inhibitors As Drugs,* McMillan & Co., Ed—M. Standler, pp 127–146, (1980). The instant compounds are considered to have antimetastatic potential in view of their platelet inhibition properties.

The pharmacological properties of the instant compounds can be demonstrated by conventional in vitro and in vivo biological tests such as the following.

IN VITRO INHIBITION OF PLATELET AGGREGATION

The aggregometer method of Born (1), as modified by Mustard, et al. (2) was used to assess the in vitro activity of the various compounds as to inhibition of adenosine diphosphate (ADP) and collagen-induced platelet aggregation. Platelet rich plasma (PRP) was separated by centrifugation from citrated (3.8 percent) rabbit blood. ADP in final concentration of 0.5 mcg/ml or 0.05 ml of a collagen suspension prepared according to the method described by Evans, et al. (3) was used to induce aggregation. The various compounds tested were dissolved in dimethylsulfoxide (DMSO) so that 5 mcl added to the platelet rich plasma would yield the desired test concentration. Vehicle control trials were done and compared with aggregation induced in platelet rich plasma containing various concentrations of the test compounds. Dose response curves were obtained and Effective Concentration (EC50) values calculated. In this test, the $EC_{50}$ values for dipyrimidol, a clinically useful antithrombogenic agent, are >512 mcg/ml vs. ADP and 245 mcg/ml vs. collagen. Results are given in Table I hereinafter for various Formula I and XII (infra.) compounds.

1. Born, G. V. R., J. Physiol., London, 162, 67P (1962).
2. Mustard, J. F., Hegardt, B. Rowsell, H. C. and MacMillan, R. L., J. Lab. Clin. Med., 64, 548 (1964).
3. Evans, G., Marian M. C., Packham, M. A., Nishizawa, E. E., Mustard, J. F. and Murphy, E. A., J. Exp. Med., 128, 877 (1968).

INHIBITION OF PLATELET AGGREGATION FOLLOWING ORAL ADMINISTRATION

This test is sometimes referred to in the art as an Ex vivo method and was initially described by Fleming, et al., *Arch. Int. Pharmacodyn. Ther.*, 199, 164 (1972). Briefly, the assay is essentially carried out as follows.

Aggregometry is performed in vitro as previously described on platelet rich plasma samples obtained from rats dosed with either test compounds or the vehicle. In all cases, activity is determined 2 hours after the drug is administered orally at various doses by gavage as a suspension in 0.9% water plus a few drops of Tween 20. Drug activity is expressed as $ED_{50}$'s (that dose required to inhibit the induced aggregation by 50%) calculated from results obtained from groups of 10 animals treated with various doses of test compounds in comparison to separate control groups.

In this test, the $ED_{50}$ of dipyridamole is greater than 100 mg/kg and anagrelide is 4.9 mg/kg. Results are given in Table I hereinafter for various Formula I and Formula XII (infra.) compounds.

INHIBITION OF CYCLIC AMP PHOSPHODIESTERASE

This assay is carried out essentially as described by Thompson, et al., *Methods in Enzymology*, 38, 205–212 (1974). Briefly, tritium labeled cyclic adenosine monophosphate (cAMP) is incubated with a phosphodiesterase (PDE) enzynme obtained from human platelets which converts a portion of the cAMP to 5'AMP in culture tubes. This reaction is terminated by submerging the tubes in a boiling water bath after which they are placed on ice and an aliquot of snake venom is added to each tube. This, during a second incubation, converts the 5'AMP to adenosine. Ion exchange resin is added to bind the remaining cyclic AMP. The tubes are centrifuged to sediment the resin and a portion of the clear supernatent (which contains radioactive adenosine) is counted in a liquid scintillation counter. The cAMP phosphodiesterase inhibition activity of a test agent is determined by pre-incubating the PDE enzyme preparation with the test agent. Dose response values are obtained and activity of the test agent reported as the molar (M) concentration of the test agent inhibiting 50% of the PDE activity ($IC_{50}$s). In this test, the $IC_{50}$ value of milrinone, a known inotropic agent, is $2 \times 10^{-7}$ molar. Results are given in Table I hereinafter for various Formula I and Formula XII (infra.) compounds.

IN VITRO INOTROPIC ACTIVITY

The basic assay is a modification of that described by Anderson, *Drug Development Research*, 3, 443–457 (1983). Briefly, guinea pigs are sacrificed by cervical disclocation and the heart rapidly exposed. Silk thread ties are placed on the left atria and these are removed from the animal and mounted in tissue baths where they are electrically driven. After an initial equilibration period, the atria are treated with propanolol at a concentration of $10^{-5}$ Molar (M). This depresses their native force of contraction but also renders them more sensitive to the positive inotropic effects of phosphodiesterase inhibitors. The ability of drugs to increase the force of contraction of the atria is assessed. Dose response curves of test compounds are obtained and reported as a percent of the propanolol control value. When desired, the chronotropic response of right atria which beat spontaneously can also be assessed. Results are given in Table II hereinafter for various Formula I and Formula XII (infra.) compounds.

IN VIVO INOTROPIC ACTIVITY

This test is carried out in ferrets as follows.

Fasted anesthetized ferrets are instrumented to study hemodynamic parameters as well as right ventricular contractile force using a Walton-Brodie open strain guage arch. Drugs are administered intraduodenally as solutions in DMSO (1 mL or less) and effects on myocardial contractile force and other parameters are monitored for 60 minutes after dosing. Changes in contractile force in response to drug treatment are expressed in terms of percent change from predose control.

In this test, milrinone produces a 52% increase in RVCF at 3 mg/kg. Results are given in Table II hereinafter for various Formula I and Formula XII (infra.) compounds.

TABLE I

Inhibition of Platelet Aggregation and cAMP Phosphodiesterase

| Example[a] | Platelet Inhibition In Vitro - Rabbit PRP $EC_{50}$ (mcg/ml) vs. ADP | vs. collagen | Ex Vivo vs. ADP $ED_{50}$ (mg/kg) | cAMP Phosphodiesterase Human Platelets $IC_{50}$ (M) |
|---|---|---|---|---|
| 1 | 0.8 | 0.2 | 12.6 | $3 \times 10^{-7}$ |
| 2 | 0.75 | 0.08 | 18.9 | $3 \times 10^{-7}$ |
| 3 | 0.08 | 0.03 | 13.3 | $3 \times 10^{-9}$ |
| 4 | 0.18 | 0.06 | 12.2 | $5 \times 10^{-8}$ |
| 5 | 0.4 | 0.125 | 14.9 | $5 \times 10^{-8}$ |
| 6 | 0.5 | 0.1 | 18.3 | $3 \times 10^{-8}$ |
| 7 | 0.1 | 0.03 | 3.2 | $1.5 \times 10^{-9}$ |
| 8 | 0.6 | 0.3 | 6.8 | $5 \times 10^{-8}$ |
| 9 | 0.15 | 0.1 | 8.4 | $1 \times 10^{-7}$ |
| 10 | 0.1 | 0.1 | 7.3 | $4 \times 10^{-8}$ |
| 11 | 0.11 | 0.09 | 32 | $2 \times 10^{-8}$ |
| 12 | 0.04 | 0.02 | 5 | $2 \times 10^{-8}$ |
| 13 | 0.13 | 0.08 |  | $6 \times 10^{-9}$ |
| 14 | 0.96 | 0.94 | 10[b] | $5 \times 10^{-9}$ |
| 22 | 0.3 | 0.2 |  | $1 \times 10^{-7}$ |
| 23 | 0.15 | 0.1 | 8.2 | $8 \times 10^{-9}$ |
| 24 | 0.25 | 0.13 |  | $2 \times 10^{-6}$ |
| 25 | 0.4 | 0.7 | >10 | $3 \times 10^{-7}$ |
| 26 | 10 | 10 |  | $7 \times 10^{-6}$ |
| 27 | 7 | 7 |  | $3 \times 10^{-6}$ |
| 28 | 4 | 3 |  | $2 \times 10^{-6}$ |
| 29 | 7 | 3 |  | $1 \times 10^{-6}$ |
| 20-3 | 0.05 | 0.03 |  | $1 \times 10^{-7}$ |
| 35 | 0.1 | 0.04 | >10 | $3 \times 10^{-8}$ |
| 36 | 20 | 12 |  | $9 \times 11^{-6}$ |

[a]Refer to examples below for compound identification.
[b]33% inhibition.

TABLE II

Inotropic Activity

| Example[a] | In Vitro Guinea Pig Atria[b] | In Vivo - Ferret % Change RVCF 3 mg/kg, i.d.[c] |
|---|---|---|
| 1 | ++ | $-6 \pm 6$ |
| 2 | + | $25 \pm 3$[d] |
| 3 | ++++ | $27 \pm 2$ |
| 4 | ++ | $-8 \pm 1$[e] |
| 5 | + | $2 \pm 2$ |
| 6 | 0 | $-12 \pm 2$[f] |
| 7 | ++++ | $24 \pm 2$ |
| 8 | 0 | $18 \pm 13$ |
| 9 | + | $17 \pm 9$ |
| 10 | 0 | $21 \pm 3$[g] |
| 11 | 0 | 6 |
| 12 | ++ | $11 \pm 4$ |
| 20-3 |  | $15 \pm 4$[h] |

[a]Refer to Examples below for compound identification.
[b]Activity - increase in contractile force
0 - Not significant at $10^{-4}$ M
+ - 50% increase at $10^{-4}$ to $10^{-5}$ M
++ - 50% increase at $10^{-5}$ to $10^{-6}$ M
+++ - 50% increase at $10^{-6}$ to $10^{-7}$ M
++++ - 50% increase below $10^{-7}$ M
[c]Mean ± standard error when number (n) more than 1.
[d]$8 \pm 6$ at 10 mg/kg
[e]2 at 10 mg/kg
[f]$12 \pm 12$ at 10 mg/kg
[g]$14 \pm 8$ at 10 mg/kg
[h]$30 \pm 5$ at 0.3 mg/kg As stated above, one aspect of this invention relates to a therapeutic method for inhibiting phosphodiesterase and blood platelet aggregation in a mammal which comprises administering a therapeutically effective amount of a compound of Formula I or Formula XII (Infra.) or a pharmaceutically acceptable salt thereof to a mammal in need of such treatment. Another aspect of this invention as stated above relates to a therapeutic method for increasing heart inotropic activity which comprises administering to a warm-blooded animal, including man, in need of such treatment a therapeutically effective amount of a compound of Formula I or Formula XII (infra.), preferably a compound selected from the group consisting of 7-fluoro-1,3-dihydro-2H-imidazo[4,5-b]quinolin-2-one 8-methyl-1,3-dihydro-2H-imidazo[4,5-b]quinolin-2-one 1,3-dihydro-7,8-dimethyl-2H-imidazo[4,5-b]quinolin-2-one 1,3-dihydro-8-chloro-7-methyl-2H-imidazo[4,5-b]quinolin-2-one 8-methyl-1,3,9,9a-tetrahydro-2H-imidazo[4,5-b]quinolin-2-one The dosage employed in the instant therapeutic methods will vary with the form of administration, the particular compound chosen, the subject being tested and the effect desired. Suitable effective doses in animals range from 0.5–30 mg/kg body weight orally and from 0.05–10 mg/kg body weight parenterally (generally characterized as subcutaneous, intramuscular, and intravenous injection). It is contemplated that the effective unit dose in man will range from 0.1 to 30 mg. and preferably from 0.5 to 20 mg. administered one to three times a day. In accordance with conventional clinical practice, the effective dose can be determined by administering a Formula I compound at a dosage substantially less than the dose of the compound which is thought to be effective and then increasing the dosage in small increments until the desired effect is achieved.

In carrying out the instant therapeutic methods, the active ingredient of Formula I and Formula XII (infra.) and pharmaceutically acceptable acid addition salts thereof are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated or coated by known techniques to delay disintegration and absorption in the gastrointestinal tract and thereby provide a sustained action over a longer period. Similarly, suspension, syrups and elixers may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectible compositions are formulated as known in the art and may contain appropriate dispersing or wetting agents and suspending agents identical or similar to those mentioned above.

The following examples are given by way of illustration and are not to be construed as limiting the invention in any way inasmuch as many variations of the invention are possible within the spirit of the invention. All temperatures are degrees centrigrade and melting points taken with a Thomas Hoover capillary apparatus are uncorrected. Conventional abbreviations are employed in reporting Nuclear Magnetic Resonance (NMR) spectral data with tetramethylsilane as internal reference and chemical shift data values in parts per million.

EXAMPLE 1

8-Chloro-1,3-dihydro-2H-imidazo[4.5-b]quinolin-2-one

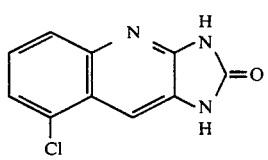

5-[(2-Chloro-6-nitrophenyl)methyl]-2,4-imidazolidinedione (2 g, 7.4 mmol) in dimethylformamide (40 mL) was hydrogenated over 10% palladium on charcoal (0.2 g) at 60 psi until hydrogen uptake ceased. The reaction mixture was heated on a steam bath for 2 hours, filtered through a pad of infusorial earth and concentrated in vacuo to give a solid. Crystallization from methanol gave hydrated 8-chloro-1,3-dihydro-2H-imidazo[4,5-b]quinolin-2-one (1.20 g, 56%), m.p. >360° C.

Anal. Calcd. for $C_{10}H_6ClN_3O \cdot 0.1H_2O$: C, 52.24; H, 2.82; N, 18.98; Cl, 16.01; $H_2O$, 0.81. Found: C, 54.18; H, 2.93; N, 18.93; Cl, 15.76; $H_2O$, 0.75.

NMR (DMSO-$d_6$): 7.44 to 7.65 (2, m); 7.69 (1, s); 7.80 (1, dd, 3 Hz, 6 Hz); 11.18 (1, bs); 11.70 (1, bs).

EXAMPLE 2

7-Fluoro-1,3-dihydro-2H-imidazo[4,5-b]quinolin-2-one

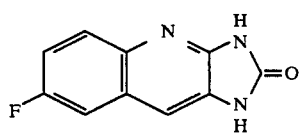

5-[(5-Fluoro-2-nitrophenyl)methyl]-2,4-imidazolidinedione (6 g, 23 mmol) in dimethylformamide (120 mL) was hydrogenated over 10% palladium on charcoal (0.6 g) at 60 psi until hydrogen uptake ceased. The reaction mixture was heated on a steam bath for 2.5 hours, filtered through a pad of infusorial earth and concentrated in vacuo to give a solid which was suspended in boiling methanol (750 mL). After 18 hours, the hot mixture was filtered and solvent evaporated to leave a solid which was dissolved in boiling methanol (500 mL) and iodine (2.0 g, 7.9 mmol) added in 2 equal portions. After 15 minutes, the solvent was evaporated and the residue treated with a solution of sodium thiosulfate (10 g) in water (100 mL) and sodium carbonate (5 g) in water (50 mL). A sandy brown solid (2.80 g) was filtered off and dissolved in dimethyl sulfoxide (30 mL). Addition of dichloromethane precipitated 7-(fluoro-1,3-dihydro-2H-imidazo[4,5-b]quinolin-2-one as a hydrate dichloromethane solvent dimethyl sulfoxide solvate (2.18 g, 45%) m.p. >360° C.

Anal. Calcd. for $C_6H_6FN_3O \cdot 0.2H_2O \cdot 0.05CH_2Cl_2 \cdot 0.05C_2H_6OS$: C, 56.72; H, 3.19; N, 19.55; $H_2O$, 1.68. Found: C, 57.01; H, 3.09; N, 19.24; $H_2O$, 1.66.

NMR (DMSO-$d_6$): 2.60 (bs,

5.74 (s, $CH_2CH_2$); 7.20-7.95 (4, m); 11.30 (2, bs).

EXAMPLE 3

8-Methyl-1,3-dihydro-2H-imidazo[4,5-b]quinolin-2-one

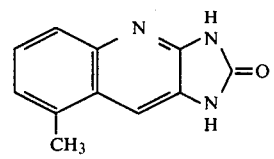

5-[(2-Methyl-6-nitrophenyl)methyl]-2,4-imidazolidinedione (5 g, 20 mmol) in dimethylformamide (200 mL) was hydrogenated over 10% palladium on charcoal (0.5 g) at 60 psi until hydrogen uptake ceased. The reaction mixture was heated on a steam bath for 2 hours, filtered through a plug of infursorial earth and the solvent evaporated. The residual solid was suspended in boiling methanol and iodine (4 g, 15 mmol) added in four equal portions over 10 minutes. The mixture was refluxed 10 minutes, concentrated in vacuo and the residue treated with a solution of sodium thiosulfate (45 g) in water (150 mL) and a solution of sodium carbonate (15 g) in water (150 mL). The insoluble solid (4.75 g) was filtered off and dissolved in 10% hydrogen chloride in methanol. Addition of ether precipitated 8-methyl-1,3-dihdyro-2H-imidazo[4,5-b]quinolin-2-one as a hydrochloride hydrate (3.38 g, 71%), m.p. 350°-355° C. (dec).

Anal. Calcd. for $C_{11}H_9N_3O \cdot HCl \cdot 0.35H_2O$: C, 54.60; H, 4.46; N, 17.37; Cl, 14.61; $H_2O$, 2.61. Found: C, 54.30; H, 4.15; N, 17.49; Cl, 14.54; $H_2O$, 0.38.

NMR (DMSO-$d_6$): 2.62 (3, s); 7.35 (1, d, 8 Hz); 7.54 (1, d, 8 Hz); 7.80 (1, s); 7.83 (1, d, 8 Hz); 9.72 (1, bs); 11.70 (1, bs).

EXAMPLE 4

7-Methyl-1,3-dihydro-2H-imidazo[4,5-b]quinolin-2-one

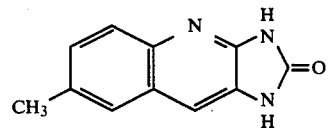

5-[(5-Methyl-2-nitrophenyl)methyl]-2,4-imidazolidinedione (5 g, 20 mmol) in dimethylformamide (200 mL) was hydrogenated over 10% palladium on charcoal (0.5 g) at 60 psi until hydrogen uptake ceased. The reaction mixture was heated on a steam bath for 2 hours, filtered through infusorial earth and concentrated in vacuo. The residual solid was treated with boiling methanol (300 mL) and iodine (4 g, 15 mmol) added in 2 equal portions over 10 minutes. Reflux was continued for a further 25 minutes before the solvent was evaporated and the residue treated with a solution of sodium thiosulfate (17 g) in water (170 mL) and a solution of sodium carbonate (10 g) in water (100 mL). A light brown solid was filtered off (4.09 g) and dissolved in 10% hydrogen chloride in methanol. Addition of ether precipitated 7-methyl-1,3-dihydro-2H-imidazo[4,5-b]quinolin-2-one as a hydrochloride hydrate (3.60 g, 74%) m.p. >360°.

Anal. Calcd. for $C_{11}H_9N_3O.HCl.0.3H_2O$: C, 54.81; H, 4.43; N, 17.43; Cl, 14.71; $H_2O$, 2.24. Found: C, 55.15; H, 4.56; N, 17.16; Cl, 14.03; $H_2O$, 0.69.

NMR (DMSO-$d_6$): 2.45 (3, s); 7.44 (1, d, 8 Hz); 7.75 (2, s); 7.90 (1, d, 8 Hz); 11.00 (1, bs); 11.62 (1, bs).

EXAMPLE 5

7-Chloro-1,3-dihydro-2H-imidazo[4,5-b]quinolin-2-one

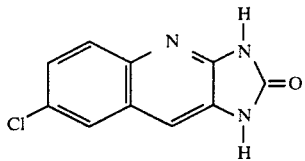

5-[(5-Chloro-2-nitrophenyl)methyl]-2,4-imidazolidinedione (3 g. 11.1 mmol) in dimethylformamide (60 mL) was hydrogenated over 10% palladium on charcoal (0.3 g) at 60 psi until hydrogen uptake ceased. The reaction mixture was heated on a steam bath for 2 hours, filtered through infusorial earth and concentrated to about 10 mL. Addition of dichloromethane furnished hydrated 7-chloro-1,3-dihydro-2H-imidazo[4,5-b]quinolin-2-one (1.22 g, 50%), m.p. >360° C.

Anal. Calcd. for $C_{10}H_6ClN_3O0.1H_2O$: C, 54.24; H, 2.82; N, 18.98; Cl, 16.01; $H_2O$, 0.81. Found: C, 54.36; H, 2.83; N, 18.88; Cl, 15.29; $H_2O$, 0.52.

NMR (DMSO-$d_6$): 7.46 (1, dd, 2 Hz, 9 Hz); 7.59 (1, s); 7.79 (1, d, 9 Hz); 7.99 (1, d, 2 Hz); 11.10 (1, bs); 11.50 (1, bs).

EXAMPLE 6

1,3-Dihydro-6,7-dimethyl-2H-imidazo[4,5-b]quinolin-2-one

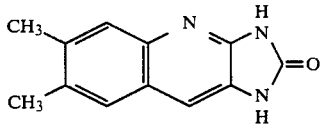

A solution of 5-[(4,5-dimethyl-2-nitrophenyl)methyl]-2,4-imidazolidinedione (3 g, 11.4 mmol) in dimethylformamide (100 mL) was hydrogenated over 10% palladium on charcoal (0.3 g) until hydrogen uptake ceased. The reaction mixture was heated on a steam bath for 3 hours before filtering through infusorial earth. Evaporation of the solvent afforded an oil which was dissolved in boiling methanol (150 mL) and treated with iodine (2 g, 7.5 mmol) in 2 equal portions over 15 minutes. After a further 15 minutes at reflux the solvent was evaporated and a solution of sodium carbonate (9 g) and sodium thiosulfate (9 g) in water (180 mL) added. A pale yellow solid was filtered off and dissolved in 10% hydrogen chloride in methanol. The solvent was evaporated and the residue crystallized from methanol to give 1,3-dihydro-6,7-dimethyl-2H-imidazo[4,5-b]quinolin-2-one as a hydrochloride hydrate (1.04 g, 47%), m.p. >360° C.

Anal. Calcd. for $C_{12}H_{11}N_3O.HCl.0.15H_2O$: C, 57.10; H, 4.91; N, 16.65; $H_2O$, 1.07. Found: C, 57.04; H, 5.01; N, 16.57; $H_2O$, 1.02.

NMR (DMSO-$d_6$): 2.36 (3, s); 2.39 (3, s); 7.70 (3, s).

EXAMPLE 7

1,3-Dihydro-7,8-dimethyl-2H-imidazo[4,5-b]quinolin-2-one

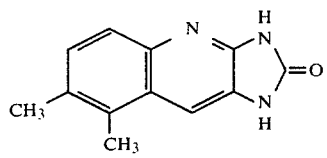

(a)

1,3-Dihydro-7,8-dimethyl-2H-imidazo[4,5-b]quinolin-2-one hydrochloride

5-[(2,3-Dimethyl-6-nitrophenyl)methyl]-2,4-imidazolidinedione (2.15 g, 8.2 mmol) in dimethylformamide (30 mL) was hydrogenated over 10% palladium on charcoal (0.2 g) at 55 psi. After 4 hours, 10% palladium on charcoal (0.2 g) was added and hydrogenation continued. After 18 hours, the reaction mixture was heated on a steam bath for 1.5 hours, cooled, filtered through infusorial earth and the solvent evaporated. The residual solid was suspended in boiling methanol (100 mL) and treated with iodine (1 g). After 30 minutes the reaction mixture was concentrated to about 30 mL and a solution of sodium thiosulfate (10 g) and sodium carbonate (10 g) in water (100 mL) added. A brown solid was filtered off, washed with water and methanol and treated with 10% hydrogen chloride in methanol. The insoluble brown solid was suspended in boiling methanol and filtered to give 1,3-dihydro-7,8-dimethyl-2H-imidazo[4,5-b]quinolin-2-one as a hydrochloride hydrate (1.0 g, 49%) m.p.>360° C.

Anal. Calcd. for $C_{12}H_{11}N_3O.HCl.0.2H_2O$: C, 56.90; H, 4.93; N, 16.59; $H_2O$, 1.42. Found: C, 57.01; H, 4.89; N, 16.33; $H_2O$, 1.07.

NMR (DMSO-$d_6$/$CF_3CO_2H$): 2.41 (3, s); 2.52 (3, s); 7.59 (2, AB quartet, 9 Hz); 7.89 (1, s); 11/50 (3, bs).

(b)

1,3-Dihydro-7,8-dimethyl-2H-imidazo[4.5-b]quinolin-2-one hydrate

5-[(2,3-Dimethyl-6-nitrophenyl)-methyl]-2,4-imidazolidinedione (40.18 g, 0.15 mole) in dimethylformamide (500 mL) was hydrogenated over 10% palladium on charcoal (6 g) at 60 psi. After 66 hours, the mixture was diluted with dimethylformamide (300 mL), warmed to dissolve some precipitated material, treated with charcoal, filtered through infusorial earth and concentrated. Residual material was suspended in boiling methanol (2 liters) and iodine (38.7 g, 0.15 mole) added portionwise over a period of 30 minutes. Reflux was continued for a further 10 minutes, the mixture concentrated to approximately 400 mL and a solution of sodium thiosulfate (60 g) and sodium carbonate (60 g) in water (600 mL) added. The precipitate was collected, washed with water and methanol and then triturated with water (500 mL). The triturated solid was collected, suspended in boiling methanol (200 mL), cooling and filtered to afford hydrated 1,3-dihydro-7,8-dimethyl-2H- imidazo[4.5-b]quinolin-2-one (29.44 g, 88%), m.p.>310° C.

Anal. Calcd. for $C_{12}H_{11}N_3O.0.2H_2O$: C, 66.47; H, 5.30; N, 19.38; $H_2O$, 1.66. Found: C, 66.14; H, 5.12; N, 19.32; $H_2O$, 1.0.

NMR (DMSO-$d_6$): 2.41 (3, s); 2.49 (3, s); 7.45 (2, AB quartet, 9 Hz); 7.62 (1, s); 10.90 (1, s); 11.30 (1, bs).

EXAMPLE 8

1,3-Dihydro-7-chloro-6-methyl-2H-imidazo[4,5-b]quinolin-2-one

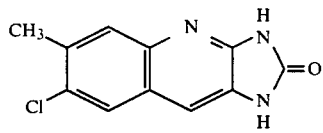

5-[(5-Chloro-4-methyl-2-nitrophenyl)methyl]-2,4-imidazolidinedione (2 g, 7 mmol) in dimethylformamide (30 mL) was hydrogenated over 5% platinum on carbon (0.4 g) at 55 psi until hydrogen uptake ceased. The mixture was heated on a steam bath for two hours, concentrated in vacuo and the residue treated with hot (90° C.) dimethyl sulfoxide. Filtration through infusorial earth and evaporation of the solvent afforded a solid which was washed with ether and suspended in boiling methanol. Filtration gave 1,3-dihydro-7-chloro-6-methyl-2H-imidazo[4,5-b]quinolin-2-one (1.40 g, 84%) m.p.>360° C.

Anal. Calcd. for $C_{11}H_8ClN_3O$: C, 56.55; H, 3.45; N, 17.98; Cl, 15.17. Found: C, 56.34; H, 3.52; N, 17.71; Cl, 14.83.

NMR (DMSO-$d_6$): 2.45 (3, s); 7.55 (1, s); 7.72 (1, s); 7.98 (1, s).

EXAMPLE 9

1,3-Dihydro-8-methoxy-2H-imidazo[4,5-b]quinolin-2-one

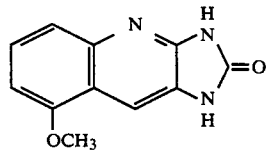

This compound was prepared analogous to Example 7(b) from 5-[(2-methoxy-6-nitrophenyl)methyl]-2,4-imidazolidinedione. The title product is obtained as a hydrate (91%), m.p.>300° C.

Anal. Calcd. for $C_{11}H_9N_3O_2.0.25H_2O$: C, 60.13; H, 4.36; N, 19.13; $H_2O$, 2.05. Found: C, 59.85; H, 4.12; N, 18.78; $H_2O$, 1.26.

NMR (DMSO-$d_6$): 3.97 (3, s); 6.88 (1, dd, 4 Hz, 5 Hz); 7.35–7.50 (2, m); 7.71 (1, s); 10.98 (1, bs); 11.45 (1, bs).

EXAMPLE 10

1,3-Dihydro-8-chloro-7-methyl-2H-imidazo[4,5-b]quinolin-2-one

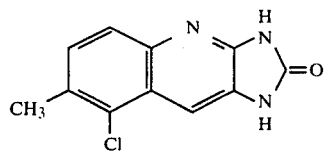

This compound was prepared analogous to Example 2 from 5-[(2-chloro-3-methyl-6-nitrophenyl)methyl]-2,4-imidazolidinedione. The title product is obtained as a hydrate (55%), m.p.>360° C.

Anal. Calcd. for $C_{11}H_8ClN_3O.0.2H_2O$: C, 55.69; H, 3.57; N, 17.71; $H_2O$, 1.52. Found: C, 54.61; H, 3.47; N, 17.11; $H_2O$, 1.43.

NMR (DMSO-$d_6$): 2.50 (3, s); 7.57 (2, AB quartet, 8 Hz); 7.69 (1, s); 11.10 (1, bs); 11.60 (1, bs).

EXAMPLE 11

7-Chloro-1,3-dihydro-6,8-dimethyl-2H-imidazo[4,5-b]quinolin-2-one

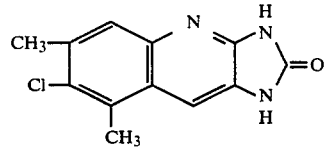

This compound was prepared analogous to Example 8 from 5-[(2,4-dimethyl-3-chloro-6-nitro)methyl]-2,4-imidazolidinedione (70%), m.p.>300° C.

Anal. Calcd. for $C_{12}H_{10}ClN_3O$: C, 58.19; H, 4.07; N, 16.97. Found: C, 57.92; H, 4.10; N, 17.03.

NMR ($CF_3CO_2H$): 2.73 (3, s); 2.93 (3, s); 7.84 (1, s); 8.90 (1, s).

EXAMPLE 12

7-Methoxy-1,3-dihydro-2H-imidazo[4,5-b]quinolin-2-one

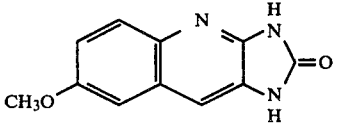

A solution of 5-[(2-nitro-5-methoxyphenyl)methylene]-2,4-imidazolidinedione (4.5 g, 17 mmol) in dimethylformamide (120 mL) was hydrogenated over 10% palladium on charcoal (0.45 g) at 60 psi. After 42 hours the mixture was filtered through infusorial earth and the solvent evaporated to leave a brown solid. A mixture of this material and methanol (150 mL) was heated to reflux and iodine (3.65 g, 14 mmol) introduced portionwise over 15 minutes. The reaction mixture was refluxed 45 minutes, cooled and concentrated to 20 mL before adding a solution of sodium thiosulfte (10 g) and sodium carbonate (10 g) in water (200 mL). The precipitate was filtered off, suspended in hot (80° C.) water (200 mL) and filtered. Recrystallization from aqueous dimethylformamide afforded 7-methoxy-1,3-dihydro- 2H-imidazo[4,5-b]quinolin-2-one (1.61 g, 43%), m.p. >360° C.

Anal. Calcd. for $C_{11}H_9N_3O_2$: C, 61.39; H, 4.22; N, 19.53. Found: C, 61.21; H, 4.27; N, 19.53.

NMR (DMSO-d6): 3.79 (3, s); 7.10 (1, dd, 3 Hz, 9 Hz); 7.28 (1, d, 3 Hz); 7.48 (1, s); 7.65 (1, d, 9 Hz); 10.90 (1, bs); 11.32 (1, bs).

EXAMPLE 13

1,3-Dihydro-6,7-dimethoxy-2H-imidazo[4,5-b]quinolin-2-one

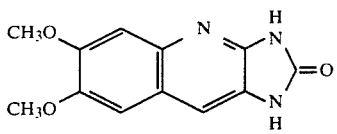

This compound was prepared analogous to Example 7(b) from 5-[(4,5-dimethoxy-2-nitrophenyl)methyl]-2,4-imidazolidinedione. The title product is obtained as a white powder (34%), m.p. >320° C.

Anal. Calcd. for $C_{12}H_{11}N_3O_3$: C, 58.77; H, 4.52; N, 17.13. Found: C, 58.38; H, 4.55; N, 17.09.

NMR (DMSO-d6): 3.88 (6, s); 7.20 (1, s); 7.30 (1, s); 7.49 (1, s); 10.50 to 11.50 (2, bs).

EXAMPLE 14

7-Bromo-1,3-dihydro-6,8-dimethyl-2H-imidazo[4,5-b]quinolin-2-one

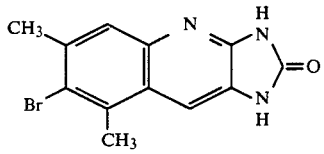

This compound was prepared analogous to Example 5 from 5-[(2,4-dimethyl-3-bromo-6-nitro)methyl]-2,4-imidazolidinedione (74%), m.p. >300° C.

Anal. Calcd. for $C_{12}H_{10}BrN_3O$: C, 49.34; H, 3.45; N, 14.38. Found: C, 49.27; H, 3.50; N, 14.42.

NMR (CF3CO2H): 2.76 (3, s); 2.98 (3, s); 7.81 (1, s); 8.90 (1, s).

EXAMPLE 15

Additional Formula I compounds are prepared by reducing the appropriately substituted hydantoin of Formula II (obtained according to Methods A or B or C) in a manner analogous to the above examples.

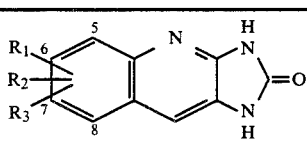

| Example No. | R1 | R2 | R3 |
|---|---|---|---|
| 15-1 | 5-CH3 | H | H |
| 15-2 | 5-CH3O | H | H |
| 15-3 | 5-Cl | H | H |
| 15-4 | 7-n-C4H7O | H | H |
| 15-5 | 7-(CH3)3CO | H | H |
| 15-6 | 7-(CH3)2CHO | H | H |
| 15-7 | 7-C2H5O | H | H |
| 15-8 | 5-CH3 | 7-CH3 | H |

-continued

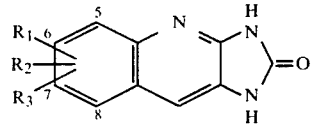

| Example No. | R1 | R2 | R3 |
|---|---|---|---|
| 15-9 | 5-CH3 | 8-CH3 | H |

EXAMPLE 16

Method A—Preparation of hydantoin intermediates of Formula II wherein a and b are hydrogen by adaptation of the method of Conners, et al. supra.

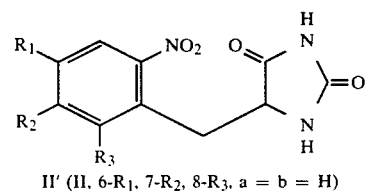

II' (II, 6-R1, 7-R2, 8-R3, a = b = H)

(a)
5-[(2,3-dimethyl-6-nitrophenyl)methyl]-2,4imidazolidinedione (R1=H, R2=R3=CH3)

Step 1. Diethyl 2-(acetylamino)-2-[(2,3-dimethyl-6-nitrophenyl)methyl]propanedioate. Sodium (3.38 g, 0.15 g atom) was dissolved in ethanol (600 mL) and diethyl acetamidomalonate (29.04 g, 0.13 mole) added in one portion. The mixture was stirred for 10 minutes and a solution of 2,3-dimethyl-6-nitrobenzyl chloride (26.70 g, 0.13 mol) in ethanol (30 mL) added. The mixture was heated under reflux for 4 hours, stirred at room temperature for 12 hours and then concentrated in vacuo. The residue was diluted with water and extracted with dichloromethane. The combined extracts were dried over sodium sulfate and the solvent evaporated to leave a viscous oil which was filtered through a plug of silica gel 6"×1⅛" using diethyl ether as eluent. The residue, after removal of the solvent was dissolved in dichloromethane and diluted with hexane to give diethyl-2-(acetylamino)-2-[(2,3-dimethyl-6-nitrophenyl)methyl]propanedioate (28.90 g, 56%). A second crop (2.3 g, 4%) was subsequently collected, m.p. 112°–113° C. Spectral data were in accord with the assigned structure.

Anal. Calcd. for $C_{18}H_{24}N_2O_7$: C, 56.84; H, 6.36; N, 7.36. Found: C, 56.79; H, 6.32; N, 7.30.

Step 2. DL-2,3-dimethyl-6-nitrophenylalanine hydrochloride. A mixture of diethyl 2-(acetylamino)-2-[(2,3-dimethyl-6-nitrophenyl)methyl]propanedioate (28.75 g, 75 mmol), concentrated hydrochloric acid solution (150 mL) and water (150 mL) was heated under reflux. After 19 hours, the solvent was evaporated and the solid residue dissolved in methanol (about 150 mL). Addition of the diethyl ether (about 800 mL) precipitated DL-2,3-dimethyl-6-nitrophenylalanine hydrochloride hydrate (16.50 g, 79%), m.p. 215°–217° C. (dec) which exhibited spectral data in accord with the designated structure.

Anal. Calcd. for $C_{11}H_{14}N_2O_4 \cdot HCl \cdot 0.25H_2O$: C, 47.32, H, 5.60; N, 10.03; Cl, 12.70; H2O, 1.61. Found: C, 46.98; H, 5.62; N, 10.28; Cl, 12.45; H2O, 1.52.

Step 3. DL-N-(Aminocarbonyl)-2,3-dimethyl-6-nitrophenylalanine Potassium cyanate (17.5 g, 0.21 mol) was added to stirred solution of DL-2,3-dimethyl-6-nitrophenylalanine hydrochloride (15 g, 0.05 mol) in water (125 mL). The mixture was heated on a steam bath for 30 minutes, cooled and acidified with 2N hydrochloric acid solution. The precipitate was filtered off, washed with water and dried in air to give DL-N-(aminocarbonyl)-2,3-dimethyl-6-nitrophenylalanine as a hydrate (16.0 g, 100%), m.p. 223°-224° C. (dec). Spectral data were in accord with the assigned structure.

Anal. Calcd. for $C_{12}H_{15}N_3O_5 \cdot 0.2H_2O$: C, 50.60; H, 5.45; N, 14.75; $H_2O$, 1.27. Found: C, 50.45; H, 5.31; N, 15.15; $H_2O$, 1.28.

Step 4. 5-[(2,3-Dimethyl-6-nitrophenyl)methyl]-2,4-imidazolidinedione. A mixture of DL-N-(aminocarbonyl)-2,3-dimethyl-6-nitrophenylalanine hydrate (15.5 g, 50 mmol) and 10% hydrogen chloride in ethanol (200 mL) was heated at reflux for 19 hours. The reaction mixture was diluted with methanol (100 mL) and filtered to give 5-[(2,3-dimethyl-6-nitrophenyl)methyl]-2,4-imidazolidinedione (3.35 g). Concentration of the mother liquors afforded a solid which was suspended in methanol and filtered to afford a second crop (3.76 g). Total yield (7.20 g, 50%). Crystallizing a sample from methanol afforded the title intermediate analytically pure as hydrated material, m.p. 172°-174° C., which exhibited spectral data in accord with the assigned structure.

Anal. Calcd. for $C_{12}H_{13}N_3O_4 \cdot 0.2H_2O$: C, 54.01; H, 5.06; N, 15.75; $H_2O$, 1.35. Found: C, 53.90; H, 4.93; N, 15.84; $H_2O$, 1.32.

(b)
5-[(2-Chloro-6-nitrophenyl)methyl]-2,4-imidazolidinedione ($R_1=R_2=H$, $R_3=Cl$)

A mixture of DL-N-(aminocarbonyl)-2-chloro-6-nitrophenylalanine (6.15 g, 21 mmol) prepared from 2-chloro-6-nitrobenzyl chloride according to steps 1, 2 and 3 above, concentrated hydrochloric acid (70 mL) and water (70 mL) was heated on a steam bath. After 45 minutes, the mixture was cooled, filtered and the solid washed with water and dried in air to give 5-[(2-chloro-6-nitrophenyl)methyl]-2,4imidazolidinedione (4.90 g, 85%), which was used without further purification. An analytical sample was prepared by dissolving a sample of the crude material (0.6 g) in boiling ethanol (30 mL) and adding ether to precipitate pure material (0.48 g). m.p. 210°-212° C. (dec). Spectral data were in accord with the assigned structure.

Anal. Calcd. for $C_{10}H_8ClN_3O_4$: C, 44.54; H, 2.99; N, 15.58; Cl, 13.15. Found: C, 44.57; H, 3.07; N, 15.42; Cl, 13.08.

(c)
5-[(5-Fluoro-2-nitrophenyl)methyl]-2-imidazolidinedione ($R_1=R_3=H$, $R_2=F$)

Prepared from 5-fluoro-2-nitrobenzyl chloride according to the procedure of Method A, m.p. 186°-188° C. from methanol.

Anal. Calcd. for $C_{10}H_8FN_3O_4$: C, 47.44; H, 3.19; N, 16.60. Found: C, 47.14; H, 3.20; N, 16.90.

(d)
5-[(2-methyl-6-nitrophenyl)methyl]-2,4-imidazolidinedione ($R_1=R_2=H$, $R_3=CH_3$)

Prepared from 2-methyl-6-nitrobenzyl chloride according to the procedure of Method A, m.p. 225°-226° C. (dec) from ethanol.

Anal. Calcd. for $C_{11}H_{11}N_3O_4$: C, 53.01; H, 4.45; N, 16.86. Found: C, 53.14; H, 4.56; N, 16.80.

(e)
5-[(5-Methyl-2-nitrophenyl)methyl]-2,4-imidazolidinedione ($R_1=R_3=H$, $R_2=CH_3$)

Prepared from 5-methyl-2-nitrobenzyl chloride according to the procedure of Method A, m.p. 222°-225° C. (dec) from ethanol.

Anal. Calcd. for $C_{11}H_{11}N_3O_4$: C, 53.01; H, 4.45; N, 16.86. Found: Cd, 52.69; H, 4.54; N, 16.78.

(f)
5-[(5-Chloro-2-nitrophenyl)methyl]-2,4-imidazolidinedione ($R_1=R_3=H$, $R_2=Cl$)

Prepared from 5-chloro-2-nitrobenzyl chloride according to the procedure of Method A, m.p. 184°-186° C. from aqueous HCl.

Anal. Calcd. for $C_{10}H_8ClN_3O_4$: C, 44.54; H, 2.99; N, 15.58; Cl, 13.15. Found: C, 44.35; H, 3.01; N, 15.25; Cl, 13.66.

(g)
5-[(4,5-Dimethyl-2-nitrophenyl)methyl]-2,4-imidazolidinedione ($R_3=H$, $R_1=R_2=CH_3$)

Prepared from 4,5-dimethyl-2-nitrobenzyl chloride according to the procedure of Method A, m.p. 248°-149° C. (dec) from ethanol.

Anal. Calcd. for $C_{12}H_{13}N_3O_4$: C, 54.75; H, 4.98; N, 15.96. Found: C, 54.48; H, 5.11; N, 15.64.

EXAMPLE 17

METHOD B. Preparation of hydantoin intermediates of Formula II wherein a and b are hydrogen

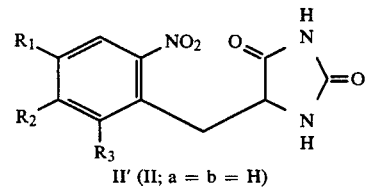

II' (II; a = b = H)

(a)
5-[(5-Chloro-4-methyl-2-nitrophyenyl)methyl]-2,4-imidazolidinedione ($R_1=CH_3$, $R_2=Cl$, $R_3=H$)

Step 1. Ethyl 4-[(5-chloro-4-methyl-2-nitrophenyl)methyl]-2,5-dioxoimidazolidine-4-carboxylate. Ethyl 2,5-dioxoimidazolidine-4-carboxylate, sodium salt (15.50 g, 80 mmol) obtained according to Garner, et al., J. Org. Chem., 20, 2003-2005 (1964) was added to a solution of 5-chloro-2-nitro benzyl chloride (17.57 g, 80 mmol) in ethanol (250 mL) and the mixture refluxed under an atmosphere of argon for 16 hours. The solvent was evaporated, the residue diluted with water and extracted with dichloromethane. The combined extracts were dried over sodium sulfate and concentrated in vacuo to afford a solid which was dissolved in dichloromethane. Addition of hexane precipitated ethyl 4-[(5- chloro-4-methyl-2-nitrophenyl)methyl]-2,5-diox-oimidazolidine-4-carboxylate (12.35 g, 43%), m.p. 176°-178° C. which exhibited spectral data in accord with assigned structure.

Anal. Calcd. for $C_{14}H_{14}ClN_3O_6$: C, 47.27; H, 3.97; N, 11.81; Cl, 9.97. Found: C, 46.95; H, 3.90; N, 11.79; Cl, 10.38.

Step 2. 5-[(5-Chloro-4-methyl-2-nitrophenyl)methyl]-2,4-imidazolidinedione. A mixture of ethyl 4-[(5-chloro-4-methyl-2-nitrophenyl)methyl]-2,5-dioxoimidazolidine 4-carboxylate (11.85 g, 33 mmol) concentrated hydrochloric acid (175 mL) and water (175 mL) was heated under reflux for 2 hours. After cooling, the precipitate was filtered off, washed with water and dried in vacuo at 78° C. to afford 5-[(5-chloro-4-methyl-2-nitrophenyl)-methyl]-2,4-imidazolidinedione (8.76 g, 95%), m.p. 211°-214° C. which displayed spectral data in accord with assigned structure.

Anal. Calcd. for $C_{11}H_{10}ClN_3O_4$: C, 46.58; H, 3.55; N, 14.81; Cl, 12.50. Found: C, 46.68; H, 3.47; N, 14.88; Cl, 12.72.

(b)

5-[(2-Methoxy-6-nitrophenyl)methyl]-2,4-imidazolidinedione ($R_1=R_2=H$, $R_3=CH_3O$)

Prepared from 2-methoxy-6-nitrobenzyl bromide according to the procedure of Method B, m.p. 193°-194° C.

Anal. Calcd. for $C_{11}H_{11}N_3O_5$: C, 49.82; H, 4.18; N, 15.84. Found: C, 49.78; H, 4.15; N, 15.91.

(c)

5-[(6-Chloro-5-methyl-2-nitrophenyl)methyl]-2,4-imidazolidinedione ($R_1=H$, $R_2=CH_3$, $R_3=Cl$)

Prepared from 2-chloro-3-methyl-6-nitrobenzyl bromide according to the procedure of Method B, m.p. 203°-205° C.

Anal. Calcd. for $C_{11}H_{10}ClN_3O_4$: C, 46.58; H, 3.55; N, 14.81. Found: C, 46.31; H, 3.53; N, 14.80.

(d)

5-[2,4-Dimethyl-3-chloro-6-nitro)methyl]-2,4-imidazolidinedione ($R_1=R_3=CH_3$, $R_2=Cl$).

Prepared from 2,4-dimethyl-3-chloro-6-nitrobenzyl bromide according to the procedure of Method B, m.p. 200°-201.5° C.

(e) 5-[(4,5-Dimethoxy-2-nitrophenyl)methyl]-2,4-imidazolidinedione ($R_1=R_2=CH_3O$, $R_3=H$).

Prepared from 4,5-dimethoxy-2-nitrobenzyl bromide according to the procedure of Method B, m.p. 207°-208° C.

Anal. Calcd. for $C_{12}H_{13}N_3O_6$: C, 48.82; H, 4.44; N, 14.23. Found: C, 48.72; H, 4.40; N, 14.31.

(f)

5-[(2,4-Dimethyl-4-bromo-6-nitro)methyl]-2,4-imidazolidinedione ($R_1=R_3=CH_3$, $R_2=Br$).

Prepared from 2,4-dimethyl-3-chloro-6-nitrobenzyl chloride according to the procedure of Method B, m.p. 199°-201° C.

EXAMPLE 18

METHOD C.—Preparation of hydantoin intermediates of Formula II wherein a and b together form a covalent bond by adaptation of the method of Billek, supra

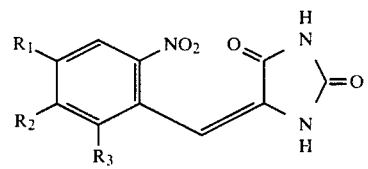

(II, 6-$R_1$, 7-$R_2$, 8-$R_3$ a + b = covalent bond)

(a)

5-[(2-Nitro-5-methoxyphenyl)methylene]-2,4-imidazolidinedione ($R_1=R_3=H$, $R_2=CH_3O$).

A mixture of 5-methoxy-2-nitrobenzaldehyde (10.0 g, 55 mmol), imidazolidine-2,4-dione (5.52 g, 55 mmol), fused sodium acetate (4.53 g, 55 mmol) and acetic anhydride (75 mL) was heated under reflux for 1 hour. The mixture was cooled and water (30 mL) added producing an exothermic reaction. The mixture was additionally diluted with water (270 mL) added portionwise over 15 minutes and then extracted with dichloromethane (2×100 mL). Combined extracts were dried over sodium sulfate and concentrated to afford the acylated 5-[(2-nitro-5-methoxyphenyl)methylene]-2,4-imidazolidinedione as an oil which is used as follows without further purification. The oil was dissolved in methanol (150 mL) and 4N sodium hydroxide solution (150 mL) added. The reaction mixture was stirred for 1 hour, acidified to pH=2 with 2N HCl and a tan precipitate filtered off, washed with water and dried in air. This material suspended in methanol and filtered gave 5-[(2-nitro-5-methoxyphenyl)methylene]-2,4-imidazolidinedione (8.0 g, 55%), m.p. 294°-295° C. (dec.) which exhibited spectral data in accord with the assigned structure.

Anal. Calcd. for $C_{11}H_9N_3O_5$: C, 50.20; H, 3.45; N, 15.96. Found: C, 49.94; H, 3.51; N, 15.64.

EXAMPLE 19

Preparation of Formula IIA compounds wherein a and b are hydrogen

General Procedure. A solution of a Formula II nitro-hydantoin (8 mmol) in dimethylformamide (60 mL) is hydrogenated over 10% palladium-on-charcoal (0.4 g) at 60 p.s.i. After hydrogen uptake ceased, the mixture is filtered through infusorial earth and the solvent evaporated under reduced pressure. Residual material consists of the Formula IIA amino-hydantoin which can be used to provide Formula IIB compounds without further purification. If desired, residual material can be further purified by conventional methods such as trituration or crystallization from an appropriate solvent.

The compounds tabulated below can be prepared according to this procedure from the corresponding Formula II nitro-hydantoin.

TABLE III

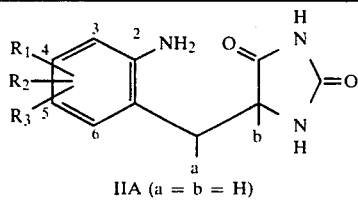

IIA (a = b = H)

| Example | R₁ | R₂ | R₃ |
|---|---|---|---|
| 19-1 | H | H | 6-Cl |
| 19-2 | H | 5-F | H |
| 19-3 | H | H | 6-CH₃ |

Triturated from diethyl ether, 90% yield, m.p. 308–310° C. (dec). NMR spectra indicates partial dimethylformamide solvate.
Anal. Calcd. for $C_{11}H_{13}N_3O_2 \cdot 0.2\ C_3H_7NO$: C, 59.58; H, 6.21; N, 19.17. Found: C, 59.30; H, 6.17; N, 18.75.

| Example | R₁ | R₂ | R₃ |
|---|---|---|---|
| 19-4 | H | 5-CH₃ | H |
| 19-5 | H | 5-Cl | H |
| 19-6 | 4-CH₃ | 5-CH₃ | H |
| 19-7 | H | 5-CH₃ | 6-CH₃ |
| 19-8 | 4-CH₃ | 5-Cl | H |
| 19-9 | H | H | 6-CH₃O |
| 19-10 | H | 5-CH₃ | 6-Cl |
| 19-11 | 4-CH₃ | 5-Cl | 6-CH₃ |
| 19-12 | H | 5-CH₃O | H |
| 19-13 | H—CH₃O | 5-CH₃O | H |
| 19-14 | 4-CH₃ | 5-Br | 6-CH₃ |

EXAMPLE 20

Preparation of 1,3,9,9a-Tetrahydro-2H-imidazo[4,5-b]quinolin-2-one Intermediates of Formula IIB General Procedure. A mixture of a Formula IIA amino-hydantoin wherein a and b are hydrogen (16 mmol) and p-toluenesulfonic acid monohydrate (0.25 g) in methanol (180 mL) is heated to reflux under an inert atmosphere (e.g. argon) for a period of 1.25 hours. Removal of the solvent under reduced pressure affords the Formula IIB tetrahydroquinoline. Purification is carried out by conventional methods such as crystallization or trituration of the residual material from solvents such as methanol, ether, and the like. If desired, acid addition salts of the Formula IIB tetrahydroquinoline can be prepared by acidifying the residual material in an appropriate solvent.

The compounds tabulated below can be prepared according to this procedure from the corresponding Formula IIA aminohydantoins wherein a and b are hydrogen.

TABLE IV

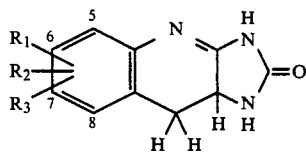

(IIB)

| Example | R₁ | R₂ | R₃ |
|---|---|---|---|
| 20-1 | H | H | 8-Cl |
| 20-2 | H | 7-F | H |
| 20-3 | H | H | 8-CH₃ |

Acidification of the residual material with methanolic hydrogen chloride and precipitation with diethyl ether provided a 62% yield of hydrated 8-methyl-1,3,9,9a-tetrahydro-2H—imidazo[4,5-b]quinolin-2-one hydrochloride, m.p. 220–225° C. (dec).
Anal. Calcd. for $C_{11}H_{11}N_3O \cdot HCl \cdot 0.55\ H_2O$: C, 53.36; H, 5.33; N, 16.97; H₂O, 4.00. Found: C, 53.03;

TABLE IV-continued

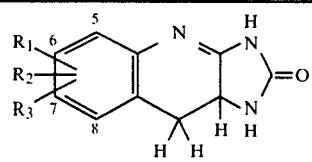

(IIB)

H, 5.44; N, 16.74; H₂O, 3.49.
NMR (DMSO-d₆): 2.29 (3,s); 2.78 (1,t, J = 15 Hz), 3.30 (1,dd, J = 15 Hz, J' = 8 Hz); 4.92 (1,dd, J = 15 Hz, J' = 8 Hz); 7.15 to 7.60 (3,m); 9.20 (1,bs); 9.80 (2,bs).

| Example | R₁ | R₂ | R₃ |
|---|---|---|---|
| 20-4 | H | 7-CH₃ | H |
| 20-5 | H | 7-Cl | H |
| 20-6 | 6-CH₃ | 7-CH₃ | H |
| 20-7 | H | 7-CH₃ | 8-CH₃ |
| 20-8 | 6-CH₃ | 7-Cl | H |
| 20-9 | H | H | 8-CH₃O |
| 20-10 | H | 7-CH₃ | 8-Cl |
| 20-11 | 6-CH₃ | 7-Cl | 8-CH₃ |
| 20-12 | H | 7-CH₃O | H |
| 20-13 | 6-CH₃O | 7-CH₃O | H |
| 20-14 | 6-CH₃ | 7-Br | 8-CH₃ |

EXAMPLE 21

Preparation of 1,3-dihydro-2H-imidazo[4,5-b]quinolin-2-ones of Formula I from 1,3,9,9a-tetrahydro2H-imidazo[4,5-b]quinolin-2-one Intermediates of Formula IIB General Procedure. Iodine (0.63 g, 2.5 mmol) is added portionwise over 30 seconds to a suspension of a Formula IIB 1,3,9,9a-tetrahydro-2H-imidazo[4,5-b]quinolin-2-one (2.5 mmol) in refluxing methanol (20 mL). The mixture is heated under reflux for 15 minutes, cooled, concentrated to approximately (5 mL) and treated with a solution of sodium thiosulfate (1 g) and sodium carbonate (1 g) in water (20 mL) with vigorous stirring. The insoluble product is collected, washed with water and dried. Other conventional purification methods can be employed such as concentrating the reaction mixture under reduced pressure and triturating the residual material with an appropriate solvent such as water, lower alkanols, etc.

If desired, acid addition salts of the Formula I products can be prepared by acidifying the residual material in an appropriate solvent. For instance, treating 8-methyl-1,3,9,9a-tetrahydro-2H-imidazo[4,5-b]quinolin-2-one with iodine as above and dissolving the insoluble product in a 10% methanolic hydrogen chloride solution followed by addition of diethyl ether provided a 72% yield of 8-methyl-1,3-dihydro-2H-imidazo[4,5-b]quinolin-2-one hydrochloride, m.p. 360°–363° C.

Anal. Calcd. for $C_{11}H_9N_3O \cdot HCl$: C, 56.06; H, 4.28; N, 17.83. Found: C, 55.95; H, 4.24; N, 17.65.

NMR (DMSO-d₆): 2.63 (3, s); 7.33 (1, d, J=8 Hz); 7.50 (1, t, J=Hz); 7.76 (1, s); 7.82 (1, d), J=8 Hz); 11.60 (1, s); 11.90 (2, bs).

FURTHER DETAILED DESCRIPTION OF THE INVENTION

Formula XII below redefines scope of the invention to include compounds of Formula I and additional compounds simlar thereto. In particular, Formula XII embodies compounds wherein the "imidazo-2-one heterocycle" fragment of Formula I is substituted with lower alkyl (preferably methyl) at the 1-position in addition to hydrogen. Further, the $R_1$ substituent has been expanded to include trifluoromethyl. Thus the present invention comprehends a compound of Formula XII

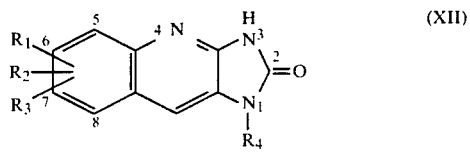
(XII)

wherein
$R_1$ is halogen, lower alkyl, lower alkoxy, trifluoromethyl;
$R_2$ is hydrogen, halogen, lower alkyl, lower alkoxy;
$R_3$ is hydrogen, halogen, lower alkyl, lower alkoxy;
$R_4$ is hydrogen, lower alkyl
or a pharmaceutically acceptable salt thereof.

It is to be understood that previously mentioned references to Formula I are to be read herein as including Formula XII compounds.

A preferred group of compounds are those of Formula XII wherein $R_1$, $R_2$ and $R_3$ are attached at the 6, 7, and 8 position, respectively, and a most preferred group are those wherein $R_1$, $R_2$ and $R_3$ are similarly attached and $R_4$ is hydrogen.

The compounds of Formula XII are obtained according to the process set forth for Formula I compounds. Thus, the compounds characterized by Formula XII

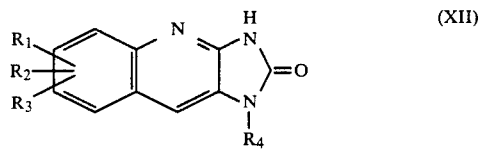
(XII)

wherein $R_1$ is halogen, lower alkyl, lower alkoxy, trifluoromethyl; $R_2$ is hydrogen, halogen, lower alkyl, lower alkoxy; $R_3$ is hydrogen, halogen, lower alkyl, lower alkoxy; and $R_4$ is hydrogen, lower alkyl, are obtained by a process comprising
(a) reducing a substituted hydantoin of Formula XIII

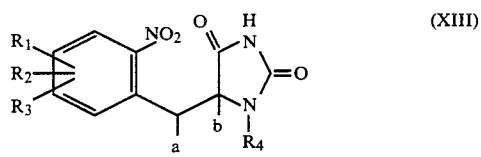
(XIII)

wherein a and b are hydrogen or together are a covalent bond, $R_1$, $R_2$, $R_3$ and $R_4$ are defined as above; and
(b) treating the reduced material with an oxidant such as iodine when required.

The foregoing process is analogous to the previously described process for reducing a Formula II hydantoin and treating reduced material with an oxidant such as iodine when required. Accordingly, reduction of Formula XIII hydantoin intermediates is carried out by conventional chemical or catalytic methods. For instance, the Formula XIII hydantoins can be chemically reduced by treatment with hydrogen iodide and red phosphorus according to the method of Kozak, et al., supra. Catalytic hydrogenation is particularly preferred and accomplished with a transition metal catalyst, preferably palladium-on-carbon, in an appropriate reaction inert solvent such as dimethylformamide. Reduction is carried out at room temperature and when hydrogen uptake is essentially complete, the reaction mixture is warmed and filtered or optionally heated to about 100° C., for a 1 to 4 hour period before filtering. In some instances, residual material obtained by concentrating the filtrate predominantly consists of the desired Formula XII product produced by facile cyclization and aratomization to the fused quinoline ring system. In other instances, the residual material predominantly consists of the uncyclized Formula XIIIA amino hydantoin (wherein a and b, $R_1$, $R_2$, $R_3$, $R_4$ are as defined above) resulting from reduction of the Formula XIII nitro hydantoin or the 4,5-dihydroquinoline intermediate of Formula XIIIB (wherein $R_1$, $R_2$, $R_3$, and $R_4$ are defined as above). In other instances, the residual material predominantly consists of a mixture of Formula XIIIA, XIIIB intermediates together with the desired Formula XII product. Without being bound by theory, the transformation of a Formula XIII nitro-hydantoin to the Formula XII product is thought to involve reduction of the nitro group and olefenic double bond to the corresponding Formula XIIIA amine (wherein a and b are hydrogen). Ring cyclization follows or occurs simultaneously to the Formula XII product or the 1,3,9,9a-tetrahydroquinoline intermediate of Formula XIIIB which is aromatized by dehydrogenation.

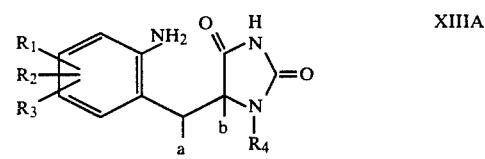
XIIIA

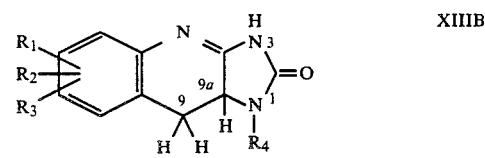
XIIIB

In those cases where the reaction is incomplete, the residual material is treated with an oxidant such as iodine in an alkanol solvent such as methanol or dimethylformamide and the like at reflux temperature. Under these conditions, cyclization of Formula XIIIA amines to the Formula XII products or the Formula XIIIB tetrahydroquinoline intermediates with oxidation of the latter to the desired 1,3-dihydro-2H-imidazo[4,5-b]quinolin-2-ones of Formula XII is effected. The Formula XIIIA and XIIIB compounds are considered part of the instant invention. When iodine is employed, the Formula XII product is isolated in base form by sequentially treating the reaction mixture with aqueous sodium thiosulfate and alkali metal carbonate such as sodium carbonate. Conversion of the base form to pharmaceutically acceptable acid addition salts is carried out by conventional means.

An alternate process for preparing Formula XII compounds comprises
(a) alkylating a thio compound of Formula XIV

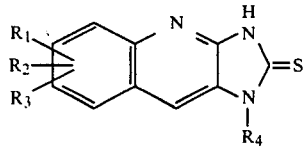

wherein $R_1$, $R_2$, $R_3$ and $R_4$ are as defined above with $R_5X$ wherein $R_5$ is lower alkyl and X represents a leaving group such as mesylate, tosylate, phosphate, sulfate and halogen, preferably chlorine or bromine to provide an alkylated thio compound of Formula XV

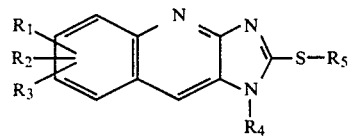

(b) and then hydrolyzing the Formula XV compound, preferably under acid conditions, to the Formula XII compound.

With reference to preparation of Formula XIII hydantoins wherein a and b represent a covalent bond, the procedure described by Billek, supra., can be used. Additionally, Formula XIII hydantoins can be obtained by reaction of a hydantoin-5-phosphonate of Formula XVI wherein $R_4$ is hydrogen or lower alkyl with a 2-nitrobenzaldehyde of Formula IX' (wherein $R_1$, $R_2$ and $R_3$ are as defined for Formula XII) illustrated in the following reaction scheme.

METHOD D

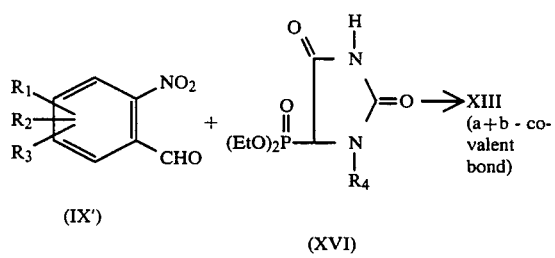

The reaction is conveniently carried out at room temperature by adding the phosphonate (XVI) to a molar equivalent of sodium dissolved in an alkanol solvent such as ethanol followed by addition of the benzaldehyde (IX' wherein $R_1$, $R_2$, $R_3$ are as defined for XIII). A relatively short period of time is required to complete the reaction (e.g. 0.5 to 2 hours) and the hydantoin (XIII wherein a+b=covalent bond) is isolated by concentrating the reaction mixture and washing the residue with water. The hydantoin derivatives (XIII wherein a+b=covalent bond) thus obtained frequently consist of a mixture of geometrical isomers wherein the predominate isomer has the vinyl proton (where present) resonating at lower field in the NMR spectrum. In the instant process for preparing Formula XII compounds from hydantoins (XIII wherein a+b=covalent bond), it is immaterial as to which isomer is used since the double bond is reduced.

With reference to preparation of Formula XIV 1,3-dihydro-2H-imidazo[4,5-b]quinolin-2-thiones, the following series of reactions are used.

METHOD E

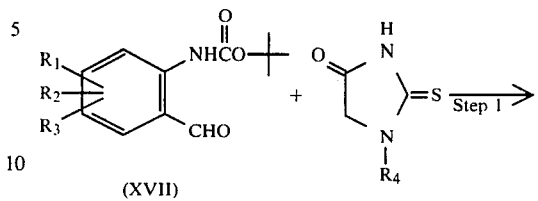

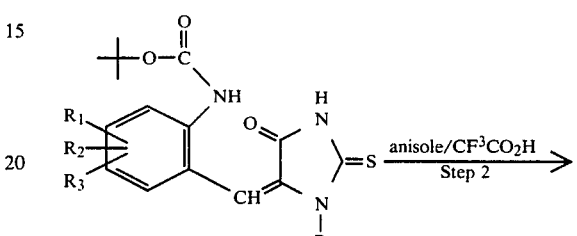

In step 1 of Method E, the aldehyde (XVII wherein $R_1$, $R_2$ and $R_3$ are as defined for XIV) is condensed with the $R_4$-2-thiohydantoin (XVIII wherein $R_4$ is hydrogen or lower alkyl) in aqueous ethanol and morpholine or piperidine at steam bath temperature. In Step 2, the amino function of (XIX) is deprotected by dissolving the material in neat trifluoro acetic acid in the presence of anisole to give the aniline intermediate (XX). Cyclization of (XIX) was effected by exposure to pyridinium tosylate in diphenyl ether at 180° C. to furnish thione (XIV).

A variation of Method E involves substituting an appropriate hydantoin for the $R_4$-thiohydantoin in Step 1 and condensing with phosphonate (XVI). Subsequent hydrolysis (Step 2) and cyclization (step 3) affords the instant compounds of Formula XII. For instance, the following series of reactions provides 1,3-dihydro-7,8-dimethyl-2H-imidazo[4,5-b]quinolin-2-one.

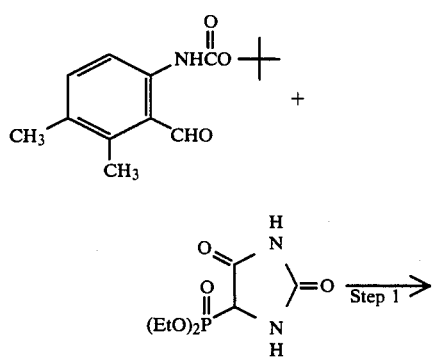

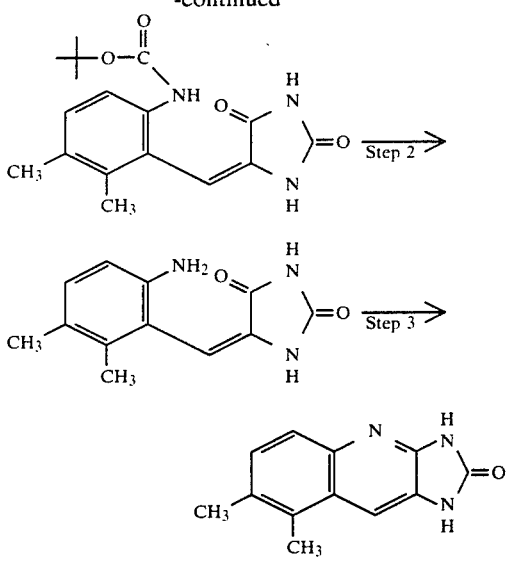

EXAMPLE 22

7-Bromo-1,3-dihydro-2H-imidazo[4,5-b]quinolin-2-one

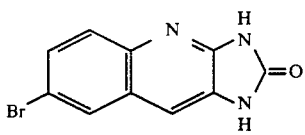

Step 1. N-[2[(2,4-Dioxo-5-imidazolidinyl)methyl]-phenyl]acetamide hydrate

N-[2-[(2,4-Dioxoimidazolidin-5-ylidene)methyl]-phenyl]acetamide obtained by condensing 2-acetamidobenzaldehyde with phosphonate (XVI) (47 g, 0.19 mole) in dimethylformamide (400 mL) was hydrogenated at 50° p.s.i. over 10% palladium on charcoal (3 g). After 7 hours, the mixture was filtered through kieselguhr, the solvent evaporated and the residue triturated with water (100 mL). After standing overnight at 5° C., the solid was collected by filtration, washed with cold water and dried in vacuo at 80° C. to give N-[2-[(2,4-dioxo-5-imidazolidinyl)methyl]phenyl]acetamide (47.15 g, 100%) which was used in Step 2 without further purification. A hydrated analytical sample purified by crystallization from aqueous ethanol had m.p. 200°–202° C.

Anal. Calcd. for $C_{12}H_{13}N_3O_3 \cdot 0.09H_2O$: C, 57.92; N, 5.34; N, 16.89; $H_2O$, 0.65. Found: C, 57.59; H, 5.38; N, 16.91; $H_2O$, 0.63.

Step 2. N-[4-Bromo-[(2,4-dioxo-5-imidazolidinyl)methyl]phenyl]acetamide

Bromine (23.26 g, 0.146 mole) in acetic acid (10 mL) was added dropwise to a stirred solution of N-[2-[(2,4-dioxo-5-imidazolidinyl)methyl]phenyl]acetamide (34.24 g, 0.139 mole) and sodium acetate (12.54 g, 0.153 mole) in acetic acid (300 mL) maintained at 65° C. The mixture was stirred at 65° C. for 18 hours during which time a heavy precipitate developed. The mixture was cooled, diluted with water (1 L) and sodium sulfite solution (added until bromine color disappears) and filtered to afford a white solid (about 17 g). The filtrate was concentrated in vacuo to afford a white solid which was triturated with water (100 mL) and filtered to give an additional 17 g of material. The combined solids were washed with diethyl ether and dried in vacuo at 50° C. to give N-[4-bromo-2-[2,4-dioxo-5-imidazolidinyl)methyl]phenyl]acetamide (30.78 g, 94%) which was used in Step 3 without further purification. An analytical sample prepared by crystallization from ethanol had m.p. 216°–220° C.

Anal. Calcd. for $C_{12}H_{12}BrN_3O_3$: C, 44.19; H, 3.71; N, 12.88. Found: C, 44.30; H, 3.79; N, 12.84.

Step 3. 5-[(2-Amino-5-bromophenyl)methyl]-2,4-imidazolidinedione

A mixture of N-[4-bromo-2-[(2,4-dioxo-5-imidazolidinyl)methyl]phenyl]acetamide (30.78 g, 94 mmol), ethanol (375 mL) and 10% hydrochloric acid solution (190 mL) was refluxed for 2.5 hours. The mixture was cooled to 5° C. and the solid (18.58 g) filtered off. The filtrate was concentrated in vacuo, neutralized with sodium bicarbonate solution, the precipitate filtered off and combined with ethanol (15 mL) and 10% hydrochloric acid solution (10 mL). After refluxing for 1.5 hours, the mixture was cooled and filtered to give an additional 1.95 g of material which was combined with the previously isolated material to give 5-[(2-amino-5-bromophenyl)methyl]-2,4-imidazolidinedione (20.53 g, 77%), m.p. >310° C.

Anal. Calcd. for $C_{10}H_{10}BrN_3O_2$: C, 42.28; H, 3.55; N, 14.79. Found: C, 42.10; H, 3.57; N, 14.70.

Step 4. 7-Bromo-1,3-dihydro-2H-imidazo[4,5-b]quinolin-2-one. Iodine (8.93 g, 0.35 mmole) was added in one portion to a solution of 5-[(2-amino-5-bromophenyl)methyl]-2,4-imidazolidinedione (10.00 g, 35 mmol) in dimethylformamide (150 mL) maintained at reflux. After 5 minutes, the mixture was cooled to room temperature, diluted with water (300 mL) and sodium sulfite solution added until colorless. Sodium carbonate (10%) solution was then added to pH=9 and the solid was filtered off, washed with water and ethanol and dried in vacuo at 78° C. overnight to give 7-bromo-1,3-dihydro-2H-imidazo[4,5-b]quinolin-2-one (8.45 g, 90%), m.p. >310° C.

Anal. Calcd. for $C_{10}H_6BrN_3O$: C, 45.49; H, 2.30; N, 15.92. Found: C, 45.69; H, 2.42; N, 15.85.

NMR (DMSO-d6): delta 7.61 (1H, dd, J=9 Hz, J'=2 Hz, aromatic H), 7.62 (1H, s); 7.71 (1H, d, J=9 Hz), 8.15 (1H, d, J=2 Hz).

EXAMPLE 23

1,3-Dihydro-7-(1-methylethoxy)-2H-imidazo[4,5-b]quinolin-2-one

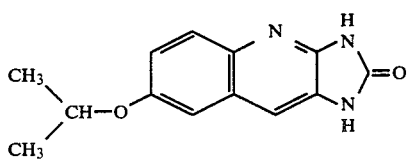

This compound (previously disclosed as Example 15-6) was prepared analogous to Example 12 from 5-[[5-(1-methylethoxy)-2-nitro]methylene]-2,4-imidazolidinedione (39%), m.p. >320° C.

Anal. Calcd. for $C_{13}H_{13}N_3O_2$: C, 64.19; H, 5.39; N, 17.27. Found: C, 64.31; H, 5.40; N, 7.11.

NMR (DMSO-d6): delta 1.34 (6H, d, J=5.5 Hz,

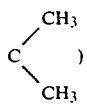

4.68 (1H, m, OCH), 7.16 (1H, d, J=9 Hz, aromatic ortho to —O—), 7.35 (1H, s), 7.59 (1H, s, aromatic H ortho to NCO), 7.76 (1H, d, J=9 Hz, aromatic H ortho to —O—), 11.04 (1H, bs, NH), 11.45 (1H, bs, NH).

EXAMPLE 24

1,3-Dihydro-6,7,8-trimethoxy-2H-imidazo[4,5-b]quinolin-2-one

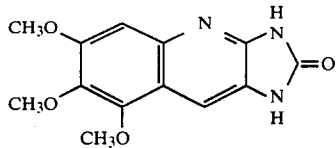

This compound is prepared analogous to Example 12 from 5-[4,5,6-trimethoxy-2-nitrophenyl)methylene]-2,4-imidazolidinedione (61% yield), m.p. >320° C.

Anal. Calcd. for $C_{13}H_{13}N_3O_4$: C, 56.73; H, 4.76; N, 15.27. Found: C, 56.90; H, 4.73; N, 15.20.

NMR (DMSO-$d_6$): delta 3.83 (3H, s, OCH$_3$), 3.90 (3H, s, OCH$_3$), 3.95 (3H, s, OCH$_3$), 7.08 (1H, s, aromatic H ortho to OCH$_3$). 7.51 (1H, s, aromatic H ortho to NCO), 10.89 (1H, s, NH) 11.42 (1H, s, NH).

EXAMPLE 25

1,3-Dihydro-6-(trifluoromethyl)-2H-imidazo[4,5-b]quinolin-2-ones

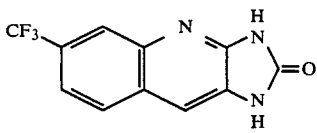

(a)
2-(Methylthio)-6-(trifluoromethyl)-1H-imidazo[4,5-b]quinolin

A suspension of 1,3-dihydro-6-(trifluoromethyl)-2H-imdazo[4,5-b]quinolin-2-thione (0.53 g, 2 mmol) in methanol (5 mL) was treated with 50% aqueous sodium hydroxide (0.18 g) to afford a solution which was cooled in an ice bath. Methyl iodide (0.3 g, 0.13 mL, 2.1 mmol) was added and the mixture stirred for 90 minutes before being filtered. The solid was washed with methanol and dried in air to give 2-(methylthio)-6-(trifluoromethyl)-1H-imidazo[4,5-b]quinoline (0.34 g, 61%), m.p. >270° C.

Anal. Calcd. for $C_{12}H_8F_3N_3S$: C, 50.88; H, 2.85; N, 14.83. Found: C, 50.50; H, 2.83; N, 15.01.

NMR (DMSO-$d_6$): delta 2.81 (3H, s, S—CH$_3$), 7.70 (1H, dd, J=8.5 Hz, J'=2 Hz, aromatic H ortho to CF$_3$), 8.29 (2H, m, aromatic H), 8.46 (1H, s, aromatic H ortho to N—C—SMe) and 13.30 (1H, bs, NH).

(b)
1,3-Dihydro-6-(trifluoromethyl)-2H-imidazo[4,5-b]quinolin-2-one

A mixture of 2-(methylthio)-6-(trifluoromethyl)-1H-imidazo[4,5-b]quinoline (1.77 g, 6 mmol), acetic acid (25 mL) and 3N hydrochloric acid solution (25 mL) was heated on a steam bath for 4 hours. The solution was diluted with hot water (250 mL), cooled and filtered. The filtrate was concentrated to afford a second crop. Solids were combined with acetic acid (25 mL) and 3N hydrochloric acid solution (25 mL) and the mixture heated on a steam bath overnight. The mixture was diluted with hot water (250 mL), cooled, the solid collected and dried in vacuo to accord 1,3-dihydro-6-(trifluoromethyl)-2H-imidazo[4,5-b]quinolin-2-one (1.38 g, 83%), m.p. >250° C.

Anal. Calcd. for $C_{11}H_6F_3N_3O$: C, 52.18; H, 2.39; N, 16.60. Found: C, 52.04; H, 2.43; N, 16.64.

EXAMPLE 26

1,3-Dihydro-1,8-dimethyl-2H-imidazo[4,5-b]quinolin-2-one

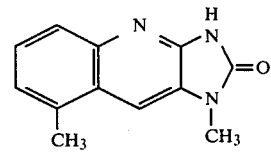

This compound obtained as a partially hydrated hydrochloride salt was prepared analogous to Example 7b from 1-methyl-5-[(2-methyl-6-nitrophenyl)methylene]-2,4-imidazolidinedione (49% yield), m.p. 340°–341° C. (dec.).

Anal. Calcd. for $C_{12}H_{11}N_3O.HCl.0.1H_2O$: C, 57.31; H, 4.89; N, 16.71. Found: C, 57.11; H, 4.75; N, 16.57.

NMR (DMSO-$d_6$): delta 2.66 (3H, s, aromatic CH$_3$), 3.41 (3H, s, N—CH$_3$), 7.29 (1H, d, J=7 Hz, aromatic H ortho to CH$_3$), 7.45 (1H, t, J=7 Hz, aromatic H meta to CH$_3$), 7.71 (1H, d, J=7 Hz, aromatic H para to CH$_3$), 7.87 (1H, s, aromatic H ortho to NH.CO).

EXAMPLE 27

1,3-Dihydro-1,7-dimethyl-2H-imidazo[4,5-b]quinolin-2-one

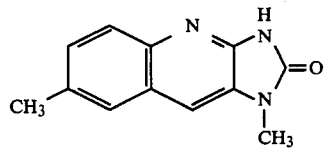

This compound is prepared analogous to Example 7b from 1-methyl-5-[(5-methyl-2-nitrophenyl)methylene]-2,4-imidazolidinedione, (46% yield), m.p. >320° C.

Anal. Calcd. for $C_{12}H_{11}N_3O.0.04H_2O$: C, 67.36; H, 5.22; N, 19.63. Found: C, 67.04; H, 5.21; N, 19.64.

NMR (DMSO-$d_6$): delta 2.46 (3H, s, aromatic CH$_3$), 3.35 (3H, s, N—CH$_3$), 7.35 (1H, d, J=7 Hz, aromatic H ortho to CH$_3$), 7.62 (1H, s, aromatic H), 7.65 (1H, s, aromatic H), 7.70 (1H, d, J=7 Hz, aromatic H meta to CH$_3$).

EXAMPLE 28

1,3-Dihydro-7-Methoxy-1-methyl-2H-imidazo[4,5-b]quinolin-2-one

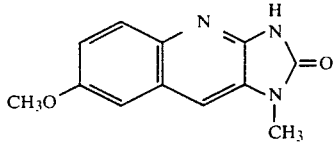

This compound obtained as a partial hydrate was prepared analogous to Example 7b from 5-[(5-methoxy-2-nitrophenyl)methylene]-1-methyl-2,4-imidazolidinedione, (54% yield), m.p. >310° C.

Anal. Calcd. for $C_{12}H_{11}N_3O_2 \cdot 0.02H_2O$: C, 62.77; H, 4.85; N, 18.30, $H_2O$, 0.157. Found: C, 62.43; H, 4.85; N, 18.14, $H_2O$, 0.094.

NMR (DMSO-$d_6$): delta 3.34 (3H, s, N$\underline{C}H_3$), 3.86 (3H, s, O$\underline{C}H_3$), 7.18 (1H, d, J=9 Hz, aromatic $\underline{H}$ ortho to O$CH_3$), 7.30 (1H, s, aromatic $\underline{H}$ ortho to O$CH_3$), 7.66 (1H, s, aromatic $\underline{H}$, s, ortho to N$\underline{H}$CO), 7.71 (1H, d, J=9 Hz, aromatic $\underline{H}$ meta to O$CH_3$).

EXAMPLE 29

1,3-Dihydro-1,7,8-trimethyl-2H-imidazo[4,5-b]quinolin-2-one

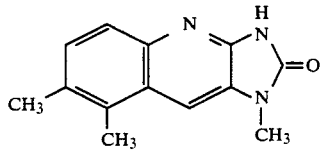

This compound was prepared analogous to Example 7b from 5-[(2,3-dimethyl-6-nitrophenyl)methylene]-2,4-imidazolidinedione, (73% yield), m.p. >300° C. (crystallized from dimethylacetamide).

Anal. Calcd. for $C_{13}H_{13}N_3O$: C, 68.70; H, 5.77; N, 18.49. Found: C, 68.36; H, 5.78; N, 18.46.

NMR (DMSO-$d_6$): delta 2.42 (3H, s, C$\underline{H}_3$), 2.55 (3H, s, C$\underline{H}_3$), 3.39 (3H, s, N—C$\underline{H}_3$), 7.34 (1H, d, J=8.5 Hz, aromatic $\underline{H}$ ortho to C$H_3$), 7.57 (1H, d, J=8.5 Hz, aromatic $\underline{H}$ meta to C$H_3$), 7.86 (1H, s, aromatic $\underline{H}$ ortho to NCO), 11.62 (1H, s, N$\underline{H}$).

EXAMPLE 30

Method D. Preparation of hydantoin intermediate of Formula XIII wherein a and b together form a covalent bond by reaction of substituted 2-nitrobenzaldehydes of Formula IX' (IX; 4-$R_1$, 5-$R_2$, 6-$R_3$) with a hydantoin-5-phosphonate

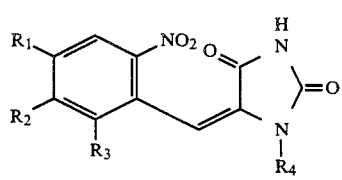

(XIII; 6-$R_1$, 7-$R_2$, 8-$R_3$, a + b = covalent bond)

(a)

5-[(2,3-Dimethyl-6-nitrophenyl)methylene]-2,3-imidazolidinedione ($R_1=R_4=H$, $R_2=R_3=CH_3$)

Sodium (0.41 g, 0.018 g atom) was dissolved in ethanol (40 mL) and diethyl 2,4-dioxoimidazolidine-5-phosphonate (4.21 g, 18 mmol) added. After 5 minutes, 2,3-dimethyl-6-nitrobenzaldehyde (2.66 g, 15 mmol) was added in one portion and the mixture stirred at room temperature for 90 minutes. The mixture was diluted with water, filtered and the solid washed with water and air dried gave 5-[(2,3-dimethyl-6-nitrophenyl)methylene]-2,4-imidazolidinedione as a single geometrical isomer (3.35 g, 86%). Analytical sample prepared by crystallization from methanol had m.p. 293°-295° C.

Anal. Calcd. for $C_{12}H_{11}N_3O_4$: C, 55.17; H, 4.24; N, 16.09. Found: C, 54.97; H, 4.27; N, 16.09.

NMR (DMSO-$d_6$): delta 2.20 (3H, s, C$H_3$), 2.37 (3H, s, C$H_3$), 6.62 (1H, s, vinyl H), 7.39 (1H, d, J=9 Hz, aromatic H).

After standing overnight, a second crop consisting of a 1.1 mixture of geometrical isomers was collected from the aqueous layer (0.5 g, 12%), m.p. 267°-270° C. (dec.).

NMR (DMSO-$d_6$): delta 2.20 (6H, s), 2.33 (3H, s), 2.37 (3H, s), 6.45 (1H, s, vinyl $\underline{H}$ trans to C=O), 6.62 (1H, s, vinyl $\underline{H}$ cis to C=O), 7.31 (1H, d, J=8 Hz), 7.38 (1H, d, J=8 Hz), 7.73 (1H, d, J=8 Hz), 7.81 (1H, d, J=8 Hz).

(b)

5-[(2-Methyl-6-nitrophenyl)methylene]-2,4-imidazolidinedione ($R_1=R_2=R_4=H$; $R_3=CH_3$)

Reaction of 2-methyl-6-nitrobenzaldehyde with diethyl 2,4-dioxoimidazolidine-5-phosphate according to the procedure of Method D provided the title compound as a single geometrical isomer, m.p. 238°-239° C. (dec.) in 81% yield.

Anal. Calcd. for $C_{11}H_9N_3O_4$: C, 53.45; H, 3.67; N, 17.00. Found: C, 53.44; H, 3.66; N, 16.92.

(c)

5-[(2,3-Dimethyl-6-nitrophenyl)methylene]-1-methyl-2,4-imidazolidinedione ($R_1=H$; $R_2=R_3=R_4=CH_3$)

Reaction of 2,3-dimethyl-6nitrobenzaldehyde with diethyl 1-methyl-2,4-dioxoimidazolidine-5-phosphonate according to the procedure of Method D provided the title compound (partial hydrate) as a mixture of geometrical isomers, m.p. 195°-198° C. in 88% yield.

Anal. Calcd. for $C_{13}H_{13}N_3O_4 \cdot 0.1H_2O$: C, 56.36; H, 4.81; N, 15.17, $H_2O$, 0.65. Found: C, 56.38; H, 4.87; N, 14.54, $H_2O$, 0.16.

(d)

5-[(5-Methoxy-2-nitrophenyl)methylene]-1-methyl-2,4-imidazolidinedione ($R_1=R_3=H$; $R_2=OCH_3$; $R_4=CH_3$)

Reaction of 3-methoxy-6-nitrobenzaldehyde with diethyl 1-methyl-2,4-dioxoimidazolidine-5-phosphonate according to the procedure of Method D provided the title compound as a mixture of geometrical isomers, m.p. 257°-260° C. in 93% yield.

Anal. Calcd. for $C_{12}H_{11}N_3O_5$: C, 51.99; H, 4.00; N, 15.16. Found: C, 51,87; H, 4.01; N, 14.90.

(e)

1-Methyl-5-[(5-methyl-2-nitrophenyl)methylene]-2,4-imidazolidinedione ($R_1=R_3=H$; $R_2=R_4=CH_3$)

Reaction of 2-methyl-6-nitrobenzaldehyde with diethyl 1-methyl-2,4-dioxoimidazolidine-5-phosphonate according to procedure of Method D provided the title compound (partial hydrate) as a mixture of geometrical isomers, m.p. 261°–262° C. in 66% yield.

Anal. Calcd. for $C_{12}H_{11}N_3O_4.0.1H_2O$: C, 54.97; H, 4.29; N, 15.97; $H_2O$, 0.68. Found: C, 54,73; H, 4.30; N, 15.62; $H_2O$, 0.24.

(f)

5-[4,5,6-Trimethoxy-2-nitrophenyl)methylene]-2,4-imidazolidinedione ($R_1=R_2=R_3=OCH_3$; $R_4=H$)

Reaction of 2,3,4-trimethoxy-6-nitrobenzaldehyde with diethyl 2,4-dioxoimidazolidine-5-phosphonate according to procedure D provides the title compound as a single geometrical isomer, m.p. 206°–208° C. in 91% yield.

Anal. Calcd. for $C_{13}H_{13}N_3O_7$: C 48.30; H, 4.05; N, 13.00. Found: C, 48.38; H, 4.02; N, 13.00.

(g)

1-Methyl-5-[(2-methyl-6-nitrophenyl)methylene]-2,4-imidazolidinedione ($R_1=R_2=H$; $R_3=R_4=CH_3$)

Reaction of 2-methyl-6-nitrobenzaldehyde with diethyl 1-methyl-2,4-dioxoimidazolidine-5-phosphonate according to procedure D provides the title compound as a mixture of geometrical isomers, m.p. 194°–197° C. in 80% yield.

Anal. Calcd. for $C_{12}H_{11}N_3O_4$: C, 55.18; H, 4.25; N, 16.09. Found: C, 54.94; H, 4.24; N, 15.82.

EXAMPLE 31

Method E. Preparation imidazo[4,5-b]quinolin-2-thiones of Formula XIV

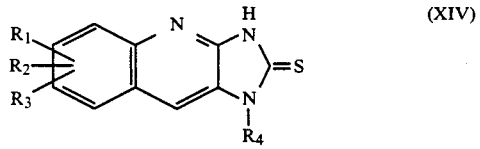

(XIV)

(a)

1,3-Dihydro-6-(trifluoromethyl)-2H-imidazo[4,5-b]quinolin-2-thione (XIV, $R_1=6$-$CF_3$, $R_2=R_3=R_4=H$)

Step 1. 1,1-Dimethyl-[2-[(5-oxo-2-thioxo-4-imidazolidinylidene)methyl]-5-(trifluoromethyl)-phenyl]carbamate.

A mixture of 1,1-dimethylethyl[2-formyl-5-(trifluoromethyl)phenyl]carbamate (20 g, 60 mmol) and 2-thiohydantoin (8.02 g, 60 mmol), ethanol (60 mL), water (60 mL) and morpholine (6 mL) was heated on a steam bath. After 90 minutes, the mixture was cooled, allowed to stand overnight and the precipitate filtered off and dried in vacuo to afford 1,1-dimethyl[2-[5-oxo-2-thioxo-4-imidazolidinylidene]methyl]-5-[(trifluoromethyl)phenyl]carbamate (20.65 g, 77%), m.p. 216° C. (dec.).

Anal. Calcd. for $C_{16}H_{16}F_3N_3O_3S$: C, 49.60; H, 4.16; N, 10.85; S, 8.27. Found: C, 49.56; H, 4.10; N, 10.92; S, 7.96.

Step 2. 5-[[2-Amino-4-(trifluormethyl)phenyl]methylene]-2-thioxo-4-imidazolidinone.

Trifluoroacetic acid (90 mL) was added to a mixture of 1,1-dimethylethyl[2-[(5-oxo-2-thioxo-4-imidazolidinylidene)methyl]-5-(trofluoromethyl)-phenylcarbamate (18 g, 46 mmol) and anisole (36 g, 0.3 mole). When solution occurred, the solvent was evaporated and the residue crystallized from a mixture of ethanol (65 mL) and chloroform (135 mL) to give 5-[[2-amino-4-(trifluoromethyl)phenyl]methylene]-2-thioxo-4-imidazolidinone (9.85 g, 73%), m.p. 240° C.

Anal. Calcd. for $C_{11}H_{18}F_3N_3OS$: C, 45.99; H, 2.81; N, 14.63. Found: C, 46.00; H, 2.81; N, 14.54.

Step 3. 1,3-Dihydro-6-(trifluoromethyl)-2H-imidazo[4,5-b]quinolin-2-thione.

A mixture of 5-[[2-amino-4-(trifluoromethyl)phenyl]-methylene]-2-thioxo-4-imidazolidinone (3.63 g, 12 mmol), pyridinium tosylate (1.8 g), and diphenyl ether (5.4 g) was heated at 180° C. under an atmosphere of argon. After 18 minutes, the mixture was cooled, chloroform (60 mL) added and the mixture refluxed. After 30 minutes the solid was filtered off and dissolved in a mixture of water (80 mL) and 10% sodium hydroxide solution (5 mL) with warming. Addition of acetic acid afforded a heavy precipitate which was filtered off, washed with water and dried in vacuo to give 1,3-dihydro-6-(trifluoromethyl)-2H-imidazo[4,5-b]quinolin-2-thione (1.79 g, 52%), m.p. >320° C.

Anal. Calcd. for $C_{11}H_6F_3N_3S$: C, 49.07; H, 2.25; N 15.61. Found: C, 48.92; H, 2.23; N, 15.58.

(b)

1,3-Dihydro-7,8-dimethyl-2H-imidazo[4,5-b]quinolin-2thione (XIV, $R_1=R_4=H$, $R_2=7$-$CH_3$, $R_3=8$-$CH_3$)

Prepared according to Method E by substituting 2-amino-5,6-dimethylbenzaldehyde for 2-amino-4-trifluorobenzaldehyde as described above in preparation of Example 31(a).

EXAMPLE 32

2,3-Dimethyl-6-nitrobenzaldehyde

Step 1. 2,3-Dimethyl-6-nitrobenzylamine.

A solution of borane-tetrahydrofuran complex (94.6 g, 1.1 mole) in tetrahydrofuran (1100 mL) was added dropwise to a stirred solution of 2,3-dimethyl-6-nitrobenzonitrile (96 g, 0.55 mole) in dry tetrahydrofuran (650 mL) maintained under an atmosphere of argon. After stirring overnight, 10% hydrochloric acid solution (1300 mL) was added dropwise and the mixture heated to reflux. After 30 minutes, the tetrahydrofuran was distilled off, the residue filtered to remove insoluble material and the filtrate made basic with concentrated ammonium hydroxide solution (350 mL). The mixture was extracted with diethyl ether (2×500 mL), the combined extracts washed with water (2×400 mL), dried over potassium carbonate and concentrated to afford 2,3-dimethyl-6-nitrobenzyl amine (93.85 g, 95%) as an oil used without further purification as follows.

Step 2. 2,3-Dimethyl-6-nitrobenzenemethanol.

Sodium nitrite (36.5 g, 0.53 mole) in water (125 ml) was added dropwise to a stirred mixture of 2,3-dimethyl-6-nitrobenzylamine (63.5 g, 0.35 mole), acetic acid (165 mL) and water (165 mL) cooled in an ice bath. After completing the addition, the mixture was stirred for 10 minutes, warmed to room temperature and stirred to a further 10 minutes before being diluted with water (1000 mL). The mixture was extracted with dichloromethane (3×500 mL), the combined extracts dried over magnesium sulfate and concentrated to afford an oil which was dissolved in methanol (400 mL). 1N Sodium hydroxide solution (400 mL) was added dropwise over 20 minutes. The methanol was removed under reduced pressure, and the residue diluted with water (1200 mL) and extracted with dichloromethane (3×700 mL). The combined extracts were dried over magnesium sulfate and the solvent evaporated to afford 2,3-dimethyl-6-nitrobenzyl alcohol (59.3 g, 93%) as brown solid used in Step 3 below without further purification. An analytical sample was prepared by crystallization from hexane/diethyl ether, m.p. 48°-51° C.

Anal. Calcd. for $C_9H_{11}NO_3$: C, 59.66; H, 6.12; N, 7.73. Found: C, 59.72; H, 6.14; N, 7.67.

Step 3. 2,3-Dimethyl-6-nitrobenzaldehyde.

A solution of 2,3-dimethyl-6-nitrobenzenemethanol (34.88 g, 0.192 mole) in dichloromethane (150 mL) was added to a stirred mixture of pyridinium chlorochromate (62.2 g, 0.288 mole) in dichloromethane (250 ml). The mixture was stirred vigorously for 4 hours, diluted with diethyl ether (500 mL) and the organic layer decanted. The residue was washed with diethyl ether (500 mL) and the combined organic solution filtered through a plug of silica gel (6"×1½"). Evaporation of the solvent afforded 2,3-dimethyl-6-nitrobenzaldehyde (32.08 g, 93%). An analytical sample was prepared by crystallizing from diisopropyl ether and had m.p. 66°-68° C.

Anal. Calcd. for $C_9H_9NO_3$: C, 60.33; H, 5.06; N, 7.82. Found: C, 60.19; H, 5.27; N, 8.27.

EXAMPLE 33

5-[((6-Amino-2,3-dimethyl)phenyl)methyl]-2,4-imidazolidinedione

5-[(2,3-Dimethyl-6-nitrophenyl)methylene]-2,4-imidazolidinedione (2.40 g, 9.2 mmol) in dimethylformamide (40 mL) was hydrogenated over 10% palladium on charcoal (0.24 g) at 60 p.s.i. in a Parr hydrogenation apparatus. After 18 hours, the mixture was filtered through infusorial earth and the solvent evaporated in vacuo at 40° C. to give the previously disclosed (Example 19-7) 5-[(6-amino-2,3-dimethylphenyl)methyl]-2,4-imidazolidinedione as a partial hydrate (2.04 g, 100%), as khaki solid, m.p. >360° C.

Anal. Calcd. for $C_{12}H_{15}N_3O_2 \cdot 0.3H_2O$: C, 60.76; H, 6.60; N, 17.35; $H_2O$, 2.82. Found: C, 60.39; H, 6.59; N, 17.61; $H_2O$, 2.26.

EXAMPLE 34

1-Methyl-5-[(2-amino-6-methylphenyl)methyl]-2,4-imidazolidinedione

Prepared from 1-methyl-5-[(2-methyl-6-nitrophenyl)methylene]-2,4-imidazolidinedione according to the procedure of Example 19.

EXAMPLE 35

7,8-Dimethyl-1,3,9,9a-tetrahydro-2H-imidazo-[4,5-b]quinolin-2-one

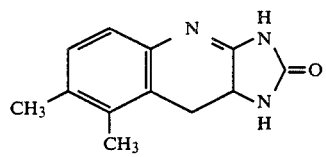

A mixture of 5-[(6-amino-2,3-dimethylphenyl)methyl]-2,4-imidazolidinedione (2.52 g, 10 mmol), p-toluenesulfonic acid (0.25 g) and methanol (50 mL) was refluxed under an atmosphere of argon for 1 hour. The mixture was cooled and a grey solid filtered off and dissolved in 10% hydrogen chloride in methanol with warming. Addition of ether afforded the previously disclosed 7,8-dimethyl-1,3,9,9a-tetrahydro-2H-imidazo[4,5-b]quinolin-2-one (Example 20-7) as the hydrochloride (1.68 g, 87%), m.p. >230° C.

Anal. Calcd. for $C_{12}H_{13}N_3O \cdot HCl$: C, 57.26; H, 5.61; N, 16.70. Found: C, 56.92; H, 5.48; N, 16.44.

NMR (DMSO-$d_6$): delta 2.20 (3H, s, $\underline{CH_3}$), 2.27 (3H, s, $\underline{CH_3}$), 2.80 (1H, t, J=14 Hz, benzylic $\underline{H}$), 3.34 (1H, dd, J=14 Hz, J'=8 Hz, benzylic H), 4.84 (1H, dd, J=14 Hz, J'=8 Hz, $\underline{CH}$.CO), 7.18 (1$\underline{H}$, d, J=9 Hz, aromatic $\underline{H}$), 7.31 (1H, d, $\overline{J}$=8 Hz, aromatic $\underline{H}$) and 9.22 (2H, s, N$\underline{H}$).

EXAMPLE 36

1,3,9,9a-Tetrahydro-1,8-dimethyl-2H-imidazo[4,5-b]quinolin-2-one

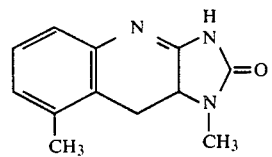

Prepared from 1-methyl-5-[(2-amino-6-methylphenyl)methyl]-2,4-imidazolidine according to the procedure of Example 20, m.p. 340°-345° C. (dec.).

Anal. Calcd. for $C_{12}H_{13}N_3O \cdot HCl$: C, 57.27; H, 5.61; N, 16.70. Found: C, 57.47; H, 5.55; N, 16.64.

EXAMPLE 37

1,3-Dihydro-7,8-dimethyl-2H-imidazo[4,5-b]quinolin-2-one

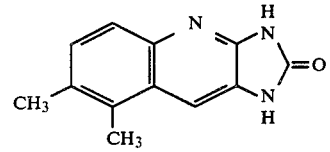

5-[(2,3-Dimethyl-6-nitrophenyl)methylene]-2,4-imidazolidinedione (19.95 g, 76 mmol) in dimethylformamide (350 mL) was hydrogenated over 10% palladium on charcoal (3 g) at 60 p.s.i. in a Parr hydrogenation apparatus. After hydrogen uptake ceased, the mixture was filtered through kieselgehr and the solvent evaporated to leave a solid which was suspended in a refluxing methanol (1 L). Iodine (19.4 g, 76 mmol) was added portionwise over 5 minutes and the mixture refluxed for 15 minutes before being concentrated in vacuo to about 100 mL. A solution of sodium thiosulfate (21 g) and sodium carbonate (11 g) in water (300 mL) was added with vigorous stirring to afford a beige precipitate which was collected, washed with water and dried in air to give 15.7 g. This was combined with crude material from experiments performed on 40 g and 4.16 g of starting material, suspended in hot (80° C.) water, filtered, suspended in refluxing methanol and filtered. Crystallization from dimethylacetamide afforded 1,3-dihydro-7,8-dimethyl-2H-imidazo[4,5-b]quinolin-2-one (53.4 g, 65%), m.p. >300° C.

Anal. Calcd. for $C_{12}H_{11}N_3O$: C, 67.59; H, 5.20; N, 19.71. Found: C, 67.28; H, 5.20; N, 19.51.

NMR (DMSO-$d_6$): delta 2.41 (3H, s, $CH_3$), 2.48 (3H, s, $CH_3$), 7.31 (1H, d, J=8 Hz, aromatic H), 7.55 (1H, d, J=8 Hz, aromatic H) and 7.61 (1H, s, aromatic H).

EXAMPLE 38

5-[(5-Ethoxy-2-nitrophenyl)methylene]-2,4-imidazolidinedione

Reaction of 2-nitro-5-ethoxybenzaldehyde with imidazolidine-2-dione according to the procedure of Method C (Example 18) provided the title compound as a single geometrical isomer, m.p. 243°–245° C. in 51% yield.

Anal. Calcd. for $C_{12}H_{11}N_3O_5$: C, 51.99; H, 4.00; N, 15.16. Found: C, 51.78; H, 4,05; N, 14.91.

EXAMPLE 39

5-[[5-(1-Methylethoxy)-2-nitro]-methylene]-2,4-imidazolidinedione

Reaction of 2-nitro-5-(1-methylethoxy)-2-benzaldehyde according to the procedure of Method C (Example 18) provided the title compound as a single geometrical isomer, m.p. 223°–230° C. in 69% yield.

Anal. Calcd. for $C_{13}H_{13}N_3O_5$: C, 53.61; H, 4.50; N, 14.43. Found: C, 53.55; H, 4.43; N, 14.25.

EXAMPLE 40

1,3-Dihydro-7-ethoxy-2H-imidazo[4,5-b]quinolin-2-one

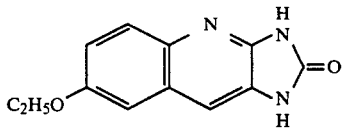

This compound (previously disclosed as Example 15-7) was prepared analogous to Example 12 from 5-[(5-ethoxy-2-nitrophenyl)methylene]-2,4-imidazolidinedione (43%), m.p. >320° C.

Anal. Calcd. for $C_{12}H_{11}N_3O_2$: C, 62.88; H, 4.84; N, 18.33. Found: C, 62.68; H, 4.92; N, 18.16.

NMR (DMSO-$d_6$): delta 1.36 (3H, t, J=7 Hz, $OCH_2CH_3$), 4.04 (2H, q, $OCH_2CH_3$), 6.97 (1H, dd, J=9 Hz, J'=2.6 Hz, aromatic H ortho to OEt), 7.08 (1H, d, J=2.6 Hz, aromatic H ortho to OEt), 7.26 (1H, s, aromatic H ortho to NCO), 7.64 (1H, d, J=9 Hz, aromatic H meta to OEt).

EXAMPLE 41

1,1-Dimethylethyl-[2-formyl-5-(trifluoromethyl)-phenyl]carbamate (a)

1,1-Dimethylethyl-[5-(trifluoromethyl)phenyl]carbonate

A mixture of 3-aminobenzotrifluoride (16 g, 0.1 mole) and di-tert-butyldicarbonate (32 g, 0.15 mole) and tetrahydrofuran (THF) (25 mL) was stirred at room temperature for 90 minutes and then heat at reflux for 90 minutes. The mixture was diluted with water (10 mL), allowed to stand overnight and concentrated in vacuo. The residue was dissolved in hexane (100 mL) at reflux, treated with activated carbon, filtered and cooled to 0° C. for 16 hours. Filtration afforded 1,1-dimethylethyl-[5-(trifluoromethyl)phenyl]carbonate (75–80% yield on several runs), m.p. 75°–76° C.

Anal. Calcd. for $C_{12}H_{14}F_3NO_2$: C, 55.17; H, 5.40; N, 5,36. Found: C, 55.13; H, 5.45; N, 5.33.

(b)

1,1-Dimethylethyl-[2-formyl-5-(trifluoromethyl)-phenyl]carbamate s-Butyllithium 15 mL of a 1.45M solution in THF (22 mmole) was added dropwise to a stirred solution of 1,1-dimethylethyl-[5-(trifluoromethyl)phenyl]carbonate (2.61 g, 10 mmole) in dry THF (40 mL) maintained at −40° C. under an atmosphere of argon. After 40 minutes, N,N-dimethylformamide (1.15 mL, 15 mmole) was added and the mixture stirred at −40° C. for 10 minutes before being diluted with diethyl ether (30 mL). The mixture was washed with 10% acetic acid solution (30 mL) and saturated sodium chloride solution (30 mL), dried over magnesium sulfate and concentrated in vacuo. The residue was chromatographed on a column of silica using a mixture of hexane and ethyl acetate (95:5) as eluent to afford 1,1-dimethylethyl-[2-formyl-5-(trifluoromethyl)phenyl]carbamate, yield 70–84%.

Anal. Calcd. for $C_{13}H_{14}F_3NO_3$: C, 53.98; H, 4.87; N, 4.84. Found: C, 53.67; H, 4.87; N, 4.85

EXAMPLE 42

Diethyl 1-Methyl-2,4-dioxoimidazolidine-5-phosphonate

A mixture of 1-methylimidazolidine-2,4-dione (202.5 g, 1.8M) and glacial acetic acid (1 L) was heated to 90° C. in an oil bath. An addition funnel was charged with bromine (311.5 g, 100 mL, 1.95M) and a small amount of bromine introduced into the reaction mixture. After dissipation of the orange color, the remainder of the bromine was added dropwise at such a rate that instant decolorization occurred. After completing the addition, the mixture was stirred at 90° C. for 60 minutes, cooled to room temperature and stirred overnight. The acetic acid was decanted from a white precipitate, concentrated in vacuo and the residue combined with the precipitate and suspended in diethyl ether (approximately 2 L). Triethyl phosphite (295 g, 320 mL, 1.8M) was added portionwise with stirring. An exothermic reaction ensued which was controlled with tap water cooling of the reaction vessel. A solution resulted which, on continued stirring, yielded a white precipitate. After standing for 60 minutes the mixture was poured into diethyl ether (4 L) and allowed to stand overnight. Filtration afforded diethyl-2-methyl-2,4-dioxoimidazolidine-5-phosphonate (331.7 g, 75%), m.p. 95°–96° C. An analytical sample crystallized from MeOH/$Et_2O$ had m.p. 95°–96° C.

Anal. Calcd. for $C_8H_{15}N_2O_5P$: C, 38.41; H, 6.04; N, 11.20. Found: 38.22; H, 6.07; N, 11.04.

The following 5-phosphonate hydantoin intermediates can be prepared analogously by substituting the appropriate imidazolidine-2,4-dione for 1-methylimidazolidine-2,4-dione in the above procedure:
diethyl 2,4-dioxoimidazolidine-5-phosphonate, m.p. 161°–163°crystallized from ethanol,
diethyl 1-ethyl-2,4-dioxoimidazolidine-5-phosphonate,
diethyl 1-propyl-2,4-dioxoimidazolidine-5-phosphonate,
diethyl 1-isopropyl-2,4-dioxoimidazolidine-5-phosphonate,
diethyl 1-butyl-2,4-dioxoimidazolidine-5-phosphonate, diethyl 1-iso-butyl-2,4-dioxoimidazolidine-5-phosphonate, diethyl 1-tert-butyl-2,4-dioxoimidazolidine-5-phosphonate.

What is claimed is:

1. A compound of the formula

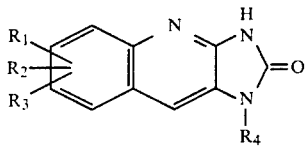

(XII)

wherein $R_1$ is halogen, lower alkyl, lower alkoxy, trifluoromethyl;

$R_2$ is hydrogen, halogen, lower alkyl, lower alkoxy;

$R_3$ is hydrogen, halogen, lower alkyl, lower alkoxy;

$R_4$ is hydrogen, lower alkyl or a pharmaceutically acceptable salt thereof.

2. The compound of claim 1 of the formula

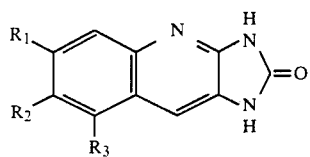

$R_1$ is halogen, lower alkyl, lower alkoxy, trifluoromethyl;

$R_2$ is hydrogen, halogen, lower alkyl, lower alkoxy;

$R_3$ is hydrogen, halogen, lower alkyl, lower alkoxy;

or a pharmaceutically acceptable salt thereof.

3. The compound of claim 1 or a pharmaceutically acceptable salt thereof which is 8-chloro-1,3-dihydro-2H-imidazo[4,5-b]quinolin-2-one.

4. The compound of claim 1 or a pharmaceutically acceptable salt thereof which is 7-fluoro-1,3-dihydro-2H-imidazo[4,5-b]quinolin-2-one.

5. The compound of claim 1 or a pharmaceutically acceptable salt thereof which is 8-methyl-1,3-dihydro-2H-imidazo[4,5-b]quinolin-2-one.

6. The compound of claim 1 or a pharmaceutically acceptable salt thereof which is 7-methyl-1,3-dihydro-2H-imidazo[4,5-b]quinolin-2-one.

7. The compound of claim 1 or a pharmaceutically acceptable salt thereof which is 7-chloro-1,3-dihydro-2H-imidazo[4,5-b]quinolin-2-one.

8. The compound of claim 1 or a pharmaceutically acceptable salt thereof which is 1,3-dihydro-6,7-dimethyl-2H-imidazo[4,5-b]quinolin-2-one.

9. The compound of claim 1 or a pharmaceutically acceptable salt thereof which is 1,3-dihydro-7,8-dimethyl-2H-imidazo[4,5-b]quinolin-2-one.

10. The compound of claim 1 or a pharmaceutically acceptable salt thereof which is 1,3-dihydro-7-chloro-6-methyl-2H-imidazo[4,5-b]quinolin-2-one.

11. The compound of claim 1 or a pharmaceutically acceptable salt thereof which is 1,3-dihydro-8methoxy-2H-imidazo[4,5-b]quinolin-2-one.

12. The compound of claim 1 or a pharmaceutically acceptable salt thereof which is 1,3-dihydro-8-chloro-7-methyl-2H-imidazo[4,5-b]quinolin-2-one.

13. The compound of claim 1 or a pharmaceutically acceptable salt thereof which is 7-chloro-1,3-dihydro-6,8-dimethyl-2H-imidazo[4,5-b]quinolin-2-one 14. The compound of claim 1 or a pharmaceutically acceptable salt thereof which is 7-methoxy-1,3-dihydro-2H-imidazo[4,5-b]quinolin-2-one.

15. The compound of claim 1 which is 1,3-dihydro-6,7-dimethoxy-2H-imidazo[4,5-b]quinolin-2-one.

16. The compound of claim 1 which is 7-bromo-1,3-dihydro-6,8-dimethyl-2H-imidazo[4,5-b]quinolin-2-one.

17. The compound of claim 1 which is 7-bromo-1,3-dihydro-2H-imidazo[4,5-b]quinolin-2-one.

18. The compound of claim 1 which is 1,3-dihydro-7-(1-methylethoxy)-2H-imidazo[4,5-b]quinolin-2-one.

19. The compound of claim 1 which is 1,3-dihydro-6,7,8-trimethoxy-2H-imidazo[4,5-b]quinolin-2-one.

20. The compound of claim 1 which is 1,3-dihydro-6-(trifluoromethyl)-2H-imidazo[4,5-b]quinolin-2-one.

21. The compound of claim 1 which is 1,3-dihydro-1,8-dimethyl-2H-imidazo[4,5-b]quinolin-2-one.

22. The compound of claim 1 which is 1,3dihydro-1,7-dimethyl-2H-imidazo[4,5-b]quinolin-2-one.

23. The compound of claim 1 which is 1,3-dihydro-7-methoxy-1-methyl-2H-imidazo[4,5-b]quinolin-2-one.

24. The compound of claim 1 which is 1,3-dihydro-1,7,8-trimethyl-2H-imidazo[4,5-b]quinolin-2-one.

25. The compound of claim 1 which is 1,3-dihydro-7-ethoxy-2H-imidazo[4,5-b]quinolin-2-one.

26. A compound of the formula

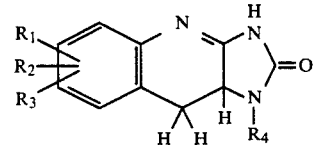

(XIIIB)

wherein $R_1$ is halogen, lower alkyl, lower alkoxy, trifluoromethyl; p1 $R_2$ is hydrogen, halogen, lower alkyl, lower alkoxy;

$R_3$ is hydrogen, halogen, lower alkyl, lower alkoxy;

$R_4$ is hydrogen, lower alkyl.

27. The compound of claim 26 which is 8-methyl-1,3,9,9a-tetrahydro-2H-imidazo[4,5-b]quinolin-2-one.

28. The compound of claim 26 which is 7,8-dimethyl-1,3,9,9a-tetrahydro-2H-imidazo[4,5-b]quinolin-2-one.

29. The compound of claim 26 which is 1,3,9,9a-tetrahydro-1,8-dimethyl-2H-imidazo[4,5-b]quinolin-2-one.

30. A compound of the formula

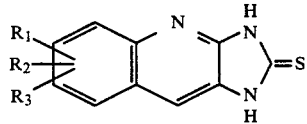

(XIV)

wherein $R_1$ is halogen, lower alkyl, lower alkoxy, trifluoromethyl;

$R_2$ is hydrogen, halogen, lower alkyl, lower alkoxy;

$R_3$ is hydrogen, halogen, lower alkyl, lower alkoxy;

$R_4$ is hydrogen, lower alkyl or a pharmaceutically acceptable salt thereof.

31. A method for inhibiting phosphodiesterase and blood platelet aggregation in a mammal which comprises administering a therapeutically effective amount of a compound of claim 1 or a pharmaceutically acceptable salt thereof.

32. A method for increasing heart inotropic activity which comprises administering to a warm blooded animal, in need of such treatment a therapeutically effective amount of a compound of claim 1 or a pharmaceutically acceptable salt thereof.

33. The pharmaceutical composition used in a method for inhibiting phosphodiesterase and blood platelet aggregation in a mammal comprised of a therapeutically effective amount in dosage unit form of a compound of claim 1 or a pharmaceutically acceptable acid addition salt thereof and a pharmaceutical carrier.

34. The pharmaceutical composition used in a method for increasing heart inotropic activity in a warm blooded animal comprised of a therapeutically effective amount in dosage unit form of a compound of claim 1 or a pharmaceutically acceptable acid addition salt thereof and a pharmaceutical carrier.

* * * * *